United States Patent
Kawamura et al.

(10) Patent No.: US 9,861,303 B2
(45) Date of Patent: Jan. 9, 2018

(54) METHOD AND APPARATUS FOR MEASURING CONCENTRATION OF TEST SUBSTANCE IN ORGANISM

(71) Applicant: Panasonic Intellectual Property Management Co., Ltd., Osaka (JP)

(72) Inventors: Tatsurou Kawamura, Kyoto (JP); Yasuaki Okumura, Kyoto (JP); Masaru Minamiguchi, Kyoto (JP); Masahiko Shioi, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 386 days.

(21) Appl. No.: 14/631,095

(22) Filed: Feb. 25, 2015

(65) Prior Publication Data

US 2015/0164393 A1 Jun. 18, 2015

Related U.S. Application Data

(63) Continuation of application No. PCT/JP2014/000205, filed on Jan. 17, 2014.

(30) Foreign Application Priority Data

Jan. 25, 2013 (JP) .................. 2013-011639

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/1451* (2013.01); *A61B 5/1455* (2013.01); *G01N 21/64* (2013.01); *G01N 21/658* (2013.01)

(58) Field of Classification Search
CPC ... A61B 5/0059; A61B 5/0205; A61B 5/1451; A61B 5/1455; A61B 5/14551; A61B 5/14552; A61B 5/14532; A61B 5/1459
See application file for complete search history.

(56) References Cited

U.S. PATENT DOCUMENTS 5,605,152 A 2/1997 Slate et al.
6,002,954 A * 12/1999 Van Antwerp ..... A61B 5/14532
600/310

(Continued)

FOREIGN PATENT DOCUMENTS

JP 08-107890 A 4/1996
JP 2003-508186 A 3/2003
(Continued)

OTHER PUBLICATIONS

Mrozek, Melissa F., et al.: "Detection and Identification of Aqueous Saccharides by Using Surface-Enhanced Raman Spectroscopy", Analytical Chemistry, vol. 74, No. 16, pp. 4069-4075, Aug. 15, 2002.
(Continued)

*Primary Examiner* — Eric Winakur
*Assistant Examiner* — Chu Chuan (JJ) Liu
(74) *Attorney, Agent, or Firm* — McDermott Will & Emery LLP

(57) ABSTRACT

An exemplary apparatus for measuring the concentration of a test substance in an organism disclosed herein includes: a measurement system which measures first and second concentrations that are concentrations of the test substance at positions A and B, respectively, where the positions A and B are located inside of the organism but outside of the blood vessel of the organism, and the position B is located more distant from the blood vessel than the position A is; and a decision circuit which determines, based on the first and second concentrations, whether or not an equilibrium has
(Continued)

been established yet between a concentration of the test substance inside of the blood vessel and a concentration of the test substance measured at a position inside of the organism but outside of the blood vessel of the organism.

16 Claims, 15 Drawing Sheets

(51) Int. Cl.
*G01N 21/64* (2006.01)
*G01N 21/65* (2006.01)

(56) References Cited

U.S. PATENT DOCUMENTS

| | | | | |
|---|---|---|---|---|
| 6,152,876 | A | * | 11/2000 | Robinson ............ A61B 5/14532 600/322 |
| 2009/0118605 | A1 | * | 5/2009 | Van Duyne ........ A61B 5/14532 600/365 |
| 2010/0309466 | A1 | * | 12/2010 | Lucassen ........... A61B 5/14532 356/303 |
| 2012/0215078 | A1 | | 8/2012 | Kawamura et al. |

FOREIGN PATENT DOCUMENTS

| | | |
|---|---|---|
| JP | 5002078 B2 | 8/2012 |
| WO | 2001-001852 A1 | 1/2001 |
| WO | 2001-018543 A1 | 3/2001 |
| WO | 2002-030275 A1 | 4/2002 |
| WO | 2005-110207 A1 | 11/2005 |
| WO | 2006-111929 A1 | 10/2006 |
| WO | 2008-143651 A2 | 11/2008 |

OTHER PUBLICATIONS

International Search Report issued in PCT/JP2014/000205, dated Feb. 18, 2014, with English translation.

* cited by examiner

METHOD AND APPARATUS FOR MEASURING CONCENTRATION OF TEST SUBSTANCE IN ORGANISM

This is a continuation of International Application No. PCT/JP2014/000205, with an international filing date of Jan. 17, 2014, which claims priority of Japanese Patent Application No. 2013-011639, filed on Jan. 25, 2013, the contents of which are hereby incorporated by reference.

BACKGROUND

1. Technical Field

The present application relates to a method and apparatus for measuring the concentration of a test substance in an organism.

2. Description of the Related Art

The concentration of a test substance (such as glucose) contained in an organism is measured, according to a known method, based on the light that has irradiated the organism and has been reflected or scattered from, or transmitted through, the organism. For example, a method for calculating the concentration of a test substance based on the radiant intensity of Raman scattered light that has been observed in the test substance is being developed.

Japanese Patent No. 5002078 (which will be hereinafter referred to as "Patent Document 1") discloses a technique for measuring highly accurately the concentration of a biogenic component such as glucose in an interstitial fluid. According to the technique, a fine particle chip including metallic nanoparticles is embedded in the dermis of an organism and is irradiated with substantially parallel light coming from outside of the organism. Then, the light produced on the fine particle chip is detected.

WO 2002/030275 (which will be hereinafter referred to as "Patent Document 2") and WO 2005/110207 (which will be hereinafter referred to as "Patent Document 3") also disclose methods for measuring the glucose concentration. According to those methods, first of all, fine particles including a reagent, of which the fluorescence property changes in reaction to glucose, are embedded in an upper layer of the skin. Next, those fine particles are irradiated with light having an excitation wavelength coming from outside of the organism, and the fluorescent light produced by the fine particles is measured percutaneously. Based on the fluorescent light measured, the glucose concentration is measured.

WO 2006/111929 discloses a method for measuring the spatial concentration gradient of a biogenic component outside of a blood vessel by irradiating a volume surrounding the blood vessel in an organism with excitation light and by detecting the light produced in the volume.

Furthermore, WO 2001/001852 (which will be hereinafter referred to as "Patent Document 4") discloses a method of detecting light produced inside an organism by irradiating the organism with light coming from outside of the organism. According to the method disclosed in Patent Document No. 4, even if the concentration of a biogenic component changes steeply, the accuracy of measuring the concentration of the biogenic component can still be maintained. According to Patent Document 4, the accuracy of measurement is maintained by establishing an equilibrium at an accelerated rate between the respective concentrations of biogenic components inside and outside of the blood vessel by heating the organism or using any other appropriate means.

SUMMARY

According to these conventional methods, however, decision cannot be made whether or not an equilibrium has been established yet between a concentration of a test substance inside of a blood vessel and a concentration of the test substance measured at a position inside of an organism but outside of its blood vessel. Thus, according to these conventional methods, if the concentration of the test substance in the blood changes steeply, the accuracy of the concentration value measured cannot be kept sufficiently high.

An exemplary embodiment of the present disclosure is an apparatus for measuring the concentration of a test substance in an organism. The apparatus includes a measurement system and a decision circuit. The measurement system measures first and second concentrations that are concentrations of the test substance at positions A and B, respectively, where the positions A and B are located inside of the organism but outside of the blood vessel of the organism, and the position B is located more distant from the blood vessel than the position A is. The decision circuit determines, based on the first and second concentrations, whether or not an equilibrium has been established yet between a concentration of the test substance inside of the blood vessel and a concentration of the test substance measured at a position inside of the organism but outside of the blood vessel of the organism.

According to an embodiment of the present disclosure, decision can be made whether or not an equilibrium has been established yet between a concentration of a test substance inside of a blood vessel and a concentration of the test substance measured at a position inside of an organism but outside of the blood vessel of the organism.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

DETAILED DESCRIPTION

Figure 1:
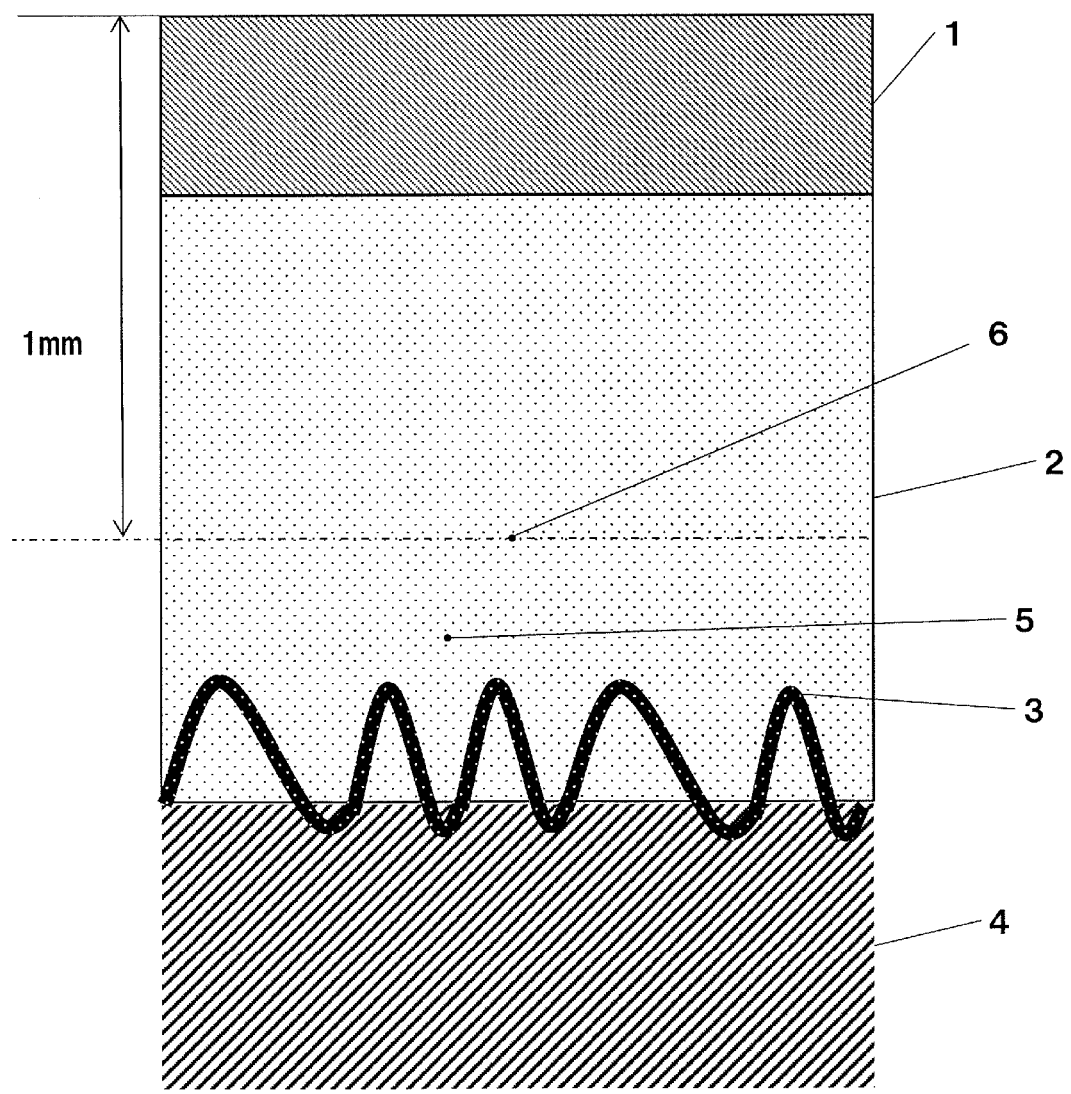
FIG. 1 is a cross-sectional view schematically illustrating an organism's skin and its subcutaneous tissue.

First of all, it will be described exactly what point the present inventors paid special attention to.

A biogenic component included in blood or urine can be extracted easily from a sample. That is why the concentration of such a biogenic component has been often measured in conventional technologies as a test substance for obtaining clinical findings. For example, a blood glucose level directly indicates the concentration of glucose in blood in the blood vessel and has been used clinically.

On the other hand, according to the techniques disclosed in Patent Documents 1, 2 and 3, fine particles are immersed in the interstitial fluid in the dermis and react to a test substance such as glucose in the interstitial fluid. By detecting the light produced by this reaction outside of the organism, the concentration of the test substance is measured and the measured value is used as a blood glucose level, for example.

As just described, the concentration in the interstitial fluid can be regarded and used as the concentration in blood. The reason is as follows. Specifically, a biogenic component such as glucose is carried by blood running through the blood vessel and supplied to skin cells. In the meantime, a biogenic component such as glucose in the blood goes through the vascular wall, diffuses through the interstitial fluid, and gets supplied to the cells. Ordinarily, the concentrations of a biogenic component such as glucose in the blood and in the interstitial fluid have reached an equilibrium state and may be regarded as substantially the same concentration. Consequently, by measuring the concentration in the interstitial fluid, this measured value may be regarded as a concentration in the blood.

However, if the concentration of a biogenic component in the blood changes so steeply, then its concentration may become significantly different between the blood and the interstitial fluid. Such a difference is made if the concentration in the blood changes before equilibrium is established again between the two concentrations. For example, the concentration of a biogenic component in the blood changes steeply when a diabetic takes in a lot of sugar at a time to cause a steep rise in blood glucose level. In an extreme example, if a diabetic takes 75 g of glucose when his or her blood glucose level is at a normal level of 100 mg/dl, his or her blood glucose level may reach as high as 250 mg/dl in 30 minutes (in that case, the blood glucose level rise rate corresponds to 5 (mg/dl)/min).

If the blood glucose level rises so steeply, then the concentration of glucose in the interstitial fluid changes in a few seconds to a few minutes after the blood glucose level has risen. That is to say, a few seconds to a few minutes after the blood glucose level has reached the maximum value, the concentration of glucose in the interstitial fluid reaches the maximum value. Also, supposing the blood glucose level is rising at a constant rate (e.g., if the rise rate is 5 (mg/dl)/min and the time delay is 1 minute), the concentration of glucose in the interstitial fluid becomes lower than the blood glucose level by 5 mg/dl. Furthermore, if the blood glucose level changes so steeply, then a spatial concentration gradient will be produced in the interstitial fluid, too. Now, it will be described with reference to FIGS. 1 and 2 how such a situation arises.

FIG. 1 schematically illustrates a cross section of epithelial and subcutaneous tissues. The epithelial tissue 1 at the surface of an organism has a thickness of approximately 0.2 to 0.5 mm. The uppermost part of this epithelial tissue 1 is a horny layer (not shown) which usually has a thickness of 10 to 20 µm. The dermis tissue 2 has a thickness of approximately 0.5 to 2.0 mm. In the dermis tissue 2, capillary blood vessels 3 are distributed. Also, in the dermis tissue 2, there is interstitial fluid which is a body fluid between tissue cells. Since the dermis tissue 2 has a huge number of capillary blood vessels 3, the interstitial fluid includes a component permeated through the walls of the capillary blood vessels. Particularly, glucose has so high permeability that an equilibrium will be established in a short time between the concentration of glucose in the interstitial fluid and the blood glucose level. Consequently, in a situation where the blood glucose level does not change steeply, the concentration of glucose in the interstitial fluid substantially agrees with the blood glucose level. The subcutaneous tissue 4 consists mostly of a fat tissue and capillary blood vessels 3 are also distributed in the subcutaneous tissue 4. The dot 5 shown in FIG. 1 indicates Position A in the dermis tissue 2 and the dot 6 shown in FIG. 1 indicates Position B in the dermis tissue 2. The distance between Position A and the capillary blood vessel 3 is shorter than the distance between Position B and the capillary blood vessel 3. The region surrounding Positions A and B is filled with the interstitial fluid.

Figure 2:
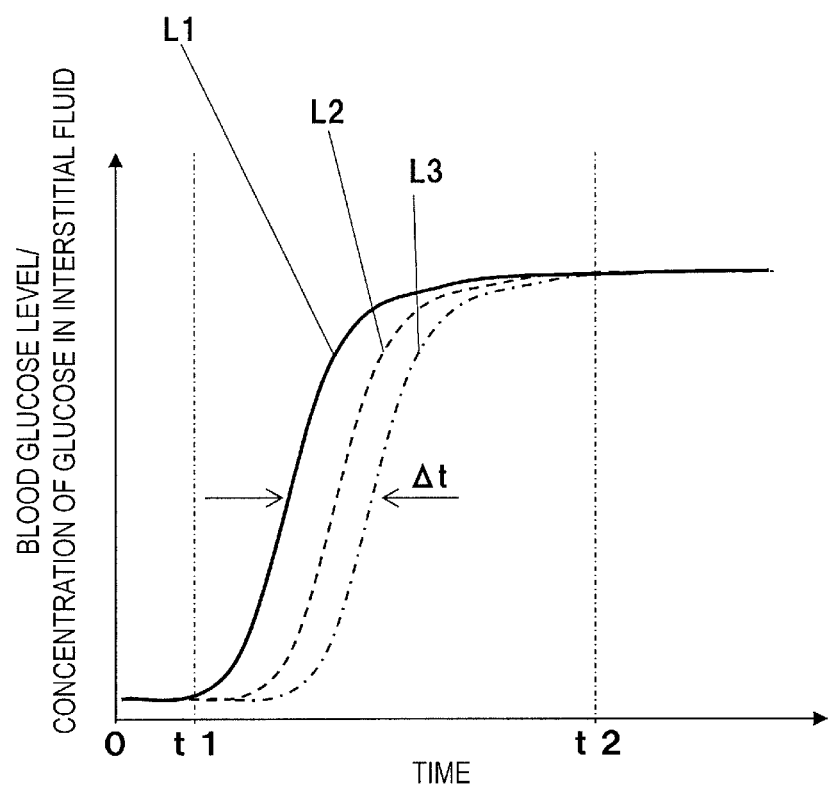
FIG. 2 is a graph generally showing how a blood glucose level and the concentration of glucose in an interstitial fluid change with time.

FIG. 2 generally shows how the blood glucose level and the concentration of glucose in the interstitial fluid change with time. In FIG. 2, the abscissa indicates the time and the ordinate indicates the blood glucose level or the concentration of glucose in the interstitial fluid. Also, in FIG. 2, the solid curve L1 represents the blood glucose level in the capillary blood vessels 3, the dotted curve L2 represents the concentration in glucose as measured at Position A in the interstitial fluid, and the one-dot chain curve L3 represents the concentration in glucose as measured at Position B in the interstitial fluid.

In FIG. 2, in the period between 0 and t1, the blood glucose level in the capillary blood vessels 3 does not change, which means that an equilibrium has been established between the blood glucose level in the capillary blood vessels 3 and the concentration of glucose in the interstitial fluid. That is to say, these two concentrations are at the same level. In the example shown in FIG. 2, the blood glucose level in the capillary blood vessels 3 starts to rise steeply at t1. At this point in time, the equilibrium state collapses, glucose starts to permeate through the vascular wall and be transported to the interstitial fluid, and the concentration of glucose in the interstitial fluid starts to rise. The concentration of glucose starts to rise at Position A earlier than at Position B. This phenomenon is observed for the following reason: since Position A is located closer to the capillary blood vessels 3 than Position B is, the glucose that has permeated through the vascular wall of the capillary blood vessels 3 and diffused through the interstitial fluid reaches Position A earlier than Position B. As the rate of increase in blood glucose level in the capillary blood vessels 3 decreases (i.e., as the blood glucose level rises less steeply), the concentration of glucose in the interstitial fluid becomes closer to the blood glucose level in the capillary blood vessels 3. And at t2, an equilibrium is reestablished between the blood glucose level in the capillary blood vessels 3 and the concentration of glucose in the interstitial fluid.

As described above, in the period between t1 and t2 in which the blood glucose level rises steeply, there is a time lag (indicated by Δt in FIG. 2) between rises in the blood glucose level and the concentration of glucose in the interstitial fluid, and a spatial concentration gradient is produced in the interstitial fluid. If there is such a time lag, an error should occur according to a method in which the concentration of glucose measured in the interstitial fluid is regarded as the blood glucose level. Consequently, the accuracy of measuring the blood glucose level would decrease.

It should be noted that the same problem will arise not only when the test substance is glucose but also when the test substance is any other substance diffusing out of the blood vessel of an organism from inside of it.

Embodiments of the present disclosure, which were devised based on such an approach, will now be described.

First of all, implementations of the present disclosure will be outlined.

A measuring apparatus according to an aspect of the present disclosure is an apparatus for measuring the concentration of a test substance in an organism. The apparatus includes measuring means and decision means. The measuring means measures first and second concentrations that are concentrations of the test substance at positions A and B, respectively, where the positions A and B are located inside of the organism but outside of the blood vessel of the organism, and the position B is located more distant from the blood vessel than the position A is. The decision means determines, based on the first and second concentrations, whether or not an equilibrium has been established yet between a concentration of the test substance inside of the blood vessel and a concentration of the test substance measured at a position inside of the organism but outside of the blood vessel of the organism.

If the difference between the first and second concentrations is less than a predetermined value, the decision means may decide that the equilibrium has already been established between the concentration of the test substance inside of the blood vessel and the concentration of the test substance measured at the position inside of the organism but outside of the blood vessel of the organism.

If the decision means decides that the equilibrium has already been established, a measured value of the first concentration may be output as the concentration of the test substance in the organism.

If the difference between the first and second concentrations is equal to or greater than a predetermined value, the decision means may decide that the equilibrium has not been established yet between the concentration of the test substance inside of the blood vessel and the concentration of the test substance measured at the position inside of the organism but outside of the blood vessel of the organism.

If the decision means decides that the equilibrium has not been established yet, notification may be made that the concentration of the test substance in the blood vessel is now changing steeply.

If the decision means decides that the equilibrium has not been established yet, a measured value of the first concentration may be output provisionally as a concentration of the test substance in the organism, and notification may be made that the measured value of the first concentration output is a provisional value.

The apparatus may further include heating means. If the decision means decides that the equilibrium has not been established yet, the heating means may heat a region surrounding the positions A and B.

A first sensor may be arranged at the position A. A second sensor may be arranged at the position B. And the measuring means may include: irradiating means for irradiating the first and second sensors with irradiating light; detecting means for detecting a first returning light beam that has returned from around the first sensor and a second returning light beam that has returned from around the second sensor; and calculating means for calculating the first and second concentrations based on the first and second returning light beams, respectively.

In each of the first and second sensors, a metal pattern may have been formed on their side to be irradiated with the irradiating light. The irradiating light may be light which induces localized surface plasmon resonance in the metal pattern. The first returning light beam may be a first surface enhanced Raman scattered light beam which has been produced in the vicinity of the metal pattern of the first sensor. The first concentration may be calculated based on the radiant intensity of the first surface enhanced Raman scattered light beam. The second returning light beam may be a second surface enhanced Raman scattered light beam which has been produced in the vicinity of the metal pattern of the second sensor. And the second concentration may be calculated based on the radiant intensity of the second surface enhanced Raman scattered light beam.

The first and second surface enhanced Raman scattered light beams may be surface enhanced Raman scattered light beams which have been produced by the test substance that is present in the vicinity of the metal pattern.

A trapping substance to trap the test substance may be immobilized on the respective metal patterns of the first and second sensors.

The first and second surface enhanced Raman scattered light beams may be surface enhanced Raman scattered light beams which have been produced by the trapping substance that is present in the vicinity of the metal pattern.

The first sensor may be a first fluorescent fine particle. The second sensor may be a second fluorescent fine particle. The first and second fluorescent fine particles may produce fluorescent light, of which the radiant intensity changes in reaction to the test substance in the organism, when irradiated with the irradiating light. The irradiating light may be light, of which the wavelength is tuned to the absorption wavelength of the first and second fluorescent fine particles. The first returning light beam may be a first fluorescent light beam which has been produced in the vicinity of the first fluorescent fine particle. The first concentration may be calculated based on the radiant intensity of the first fluorescent light beam. The second returning light beam may be a second fluorescent light beam which has been produced in the vicinity of the second fluorescent fine particle. And the second concentration may be calculated based on the radiant intensity of the second fluorescent light beam.

The first and second sensors may be embedded in the dermis of the organism.

The test substance may be glucose.

A measuring method according to another aspect of the present disclosure is a method for measuring the concentration of a test substance in an organism. The method includes the steps of: (a) measuring first and second concentrations that are concentrations of the test substance at positions A and B, respectively, where the positions A and B are located inside of the organism but outside of the blood vessel of the organism, and the position B is located more distant from the blood vessel than the position A is; and (b) determining, based on the first and second concentrations, whether or not an equilibrium has been established yet between a concentration of the test substance inside of the blood vessel and a concentration of the test substance measured at a position inside of the organism but outside of the blood vessel of the organism.

The step (b) of determining may be the step of deciding, if the difference between the first and second concentrations is less than a predetermined value, that the equilibrium has already been established between the concentration of the test substance inside of the blood vessel and the concentration of the test substance measured at the position inside of the organism but outside of the blood vessel of the organism.

If decision has been made in the step (b) of determining that the equilibrium has already been established, a measured value of the first concentration may be output as the concentration of the test substance in the organism.

The step (b) of determining may be the step of deciding, if the difference between the first and second concentrations is equal to or greater than a predetermined value, that the equilibrium has not been established yet between the concentration of the test substance inside of the blood vessel and the concentration of the test substance measured at the position inside of the organism but outside of the blood vessel of the organism.

If decision has been made, in the step (b) of determining, that the equilibrium has not been established yet, notification may be made that the concentration of the test substance in the blood vessel is now changing steeply.

If decision has been made in the step (b) of determining, that the equilibrium has not been established yet, a measured value of the first concentration may be output provisionally as a concentration of the test substance in the organism, and notification may be made that the measured value of the first concentration output is a provisional value.

If decision has been made in the step (b) of determining, that the equilibrium has not been established yet, a region surrounding the positions A and B may be heated.

A first sensor may be arranged at the position A. A second sensor may be arranged at the position B. And the step (a) of measuring may include the steps of: (a-1) irradiating the first and second sensors with irradiating light; (a-2) detecting a first returning light beam that has returned from around the first sensor and a second returning light beam that has returned from around the second sensor; and (a-3) calculating the first and second concentrations based on the first and second returning light beams, respectively.

In each of the first and second sensors, a metal pattern may have been formed on their side to be irradiated with the irradiating light. The irradiating light may be light which induces localized surface plasmon resonance in the metal pattern. The first returning light beam may be a first surface enhanced Raman scattered light beam which has been produced in the vicinity of the metal pattern of the first sensor. The first concentration may be calculated based on the radiant intensity of the first surface enhanced Raman scattered light beam. The second returning light beam may be a second surface enhanced Raman scattered light beam which has been produced in the vicinity of the metal pattern of the second sensor. And the second concentration may be calculated based on the radiant intensity of the second surface enhanced Raman scattered light beam.

The first and second surface enhanced Raman scattered light beams may be surface enhanced Raman scattered light beams which have been produced by the test substance that is present in the vicinity of the metal pattern.

A trapping substance to trap the test substance may be immobilized on the respective metal patterns of the first and second sensors.

The first and second surface enhanced Raman scattered light beams may be surface enhanced Raman scattered light beams which have been produced by the trapping substance that is present in the vicinity of the metal pattern.

The first sensor may be a first fluorescent fine particle. The second sensor may be a second fluorescent fine particle. The first and second fluorescent fine particles may produce fluorescent light, of which the radiant intensity changes in reaction to the test substance in the organism, when irradiated with the irradiating light. The irradiating light may be light, of which the wavelength is tuned to the absorption wavelength of the first and second fluorescent fine particles. The first returning light beam may be a first fluorescent light beam which has been produced in the vicinity of the first fluorescent fine particle. The first concentration may be calculated based on the radiant intensity of the first fluorescent light beam. The second returning light beam may be a second fluorescent light beam which has been produced in the vicinity of the second fluorescent fine particle. And the second concentration may be calculated based on the radiant intensity of the second fluorescent light beam.

The first and second sensors may be embedded in the dermis of the organism.

The test substance may be glucose.

A measuring apparatus controlling method according to still another aspect of the present disclosure is a method for controlling an apparatus for measuring the concentration of a test substance in an organism. The apparatus includes measuring means and decision means. The method includes the step of: (a) making the measuring means measure first and second concentrations that are concentrations of the test substance at positions A and B, respectively, where the positions A and B are located inside of the organism but outside of the blood vessel of the organism, and the position B is located more distant from the blood vessel than the position A is; and (b) making the decision means determine, based on the first and second concentrations, whether or not an equilibrium has been established yet between a concentration of the test substance inside of the blood vessel and a concentration of the test substance measured at a position inside of the organism but outside of the blood vessel of the organism.

Embodiments of the present disclosure will now be described in detail with reference to the accompanying drawings.

Figure 12:
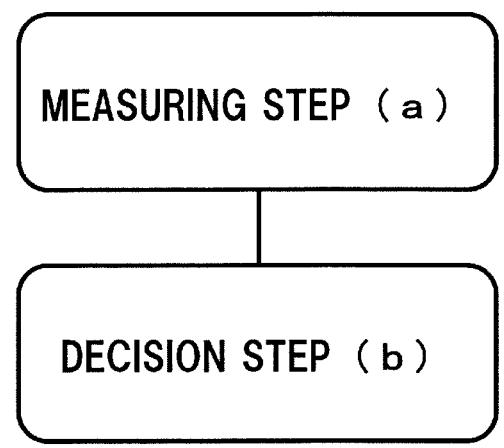
FIG. 12 is a flowchart showing an exemplary measuring method according to embodiments.

FIG. 12 is a flowchart showing an exemplary measuring method according to an embodiment.

A measuring method according to an embodiment is a method for measuring the concentration of a test substance in an organism and includes the following steps (a) and (b).

Measuring step (a): measuring first and second concentrations that are concentrations of the test substance at Positions A and B, respectively. These Positions A and B are located inside of the organism but outside of the blood vessel of the organism, and Position B is located more distant from the blood vessel than Position A is.

Decision step (b): determining, based on the first and second concentrations, whether or not an equilibrium has been established yet between a concentration of the test substance inside of the blood vessel and a concentration of the test substance measured at a position inside of the organism but outside of the blood vessel of the organism.

According to such a configuration, decision can be made whether or not an equilibrium has been established yet between a concentration of a test substance inside of a blood vessel and a concentration of the test substance measured at a position inside of an organism but outside of the blood vessel of the organism.

As a result, if the test substance is glucose, for example, it is possible to avoid the phenomenon that the accuracy of measuring the blood glucose level decreases significantly when the blood glucose level rises steeply. Consequently, a highly reliable blood glucose measured value is provided.

Typical examples of a measuring method and apparatus will now be described as first through fifth embodiments.

Embodiment 1

Figure 13:
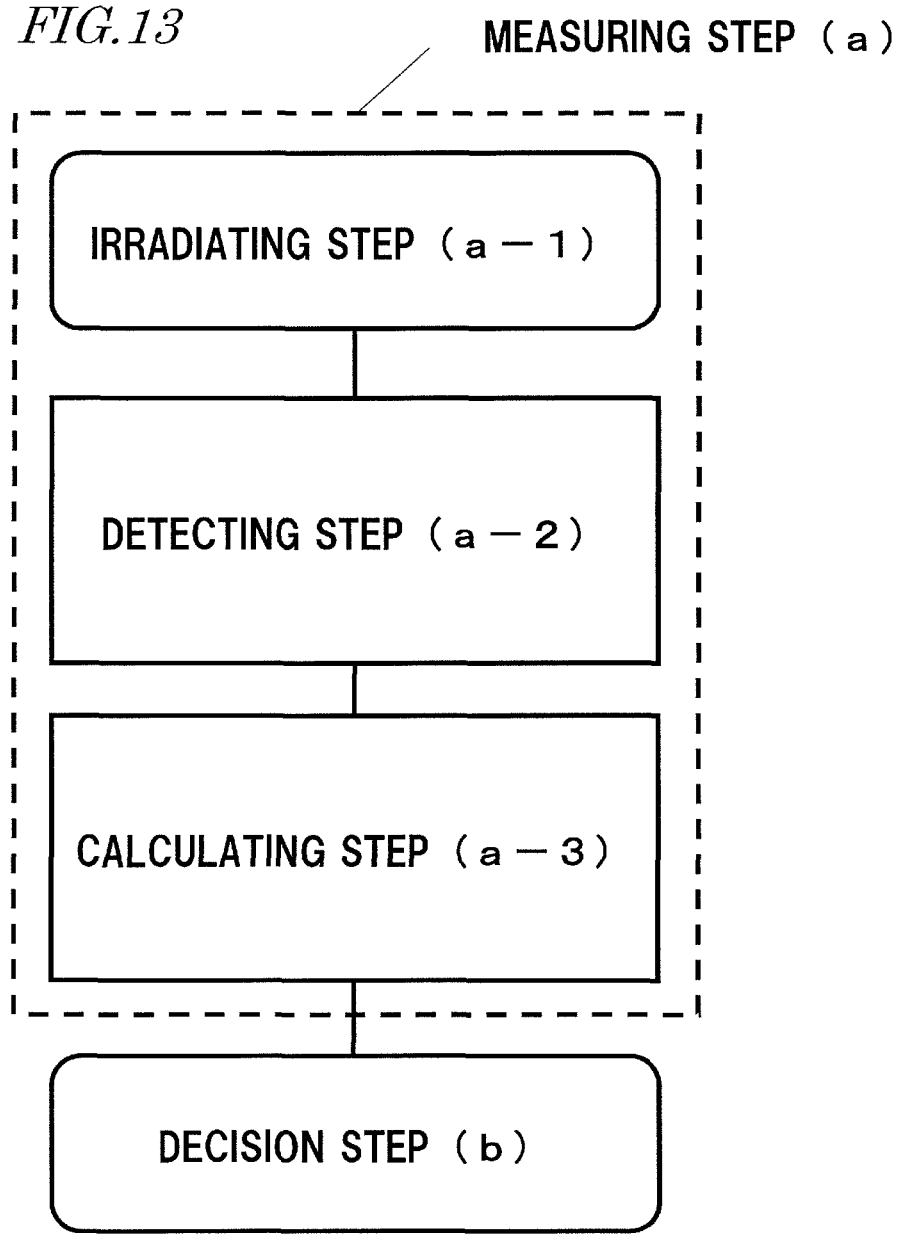
FIG. 13 is a flowchart showing an exemplary measuring method according to the first embodiment.

FIG. 13 is a flowchart showing an exemplary measuring method according to a first embodiment.

In this first embodiment, a first sensor may be arranged at Position A and a second sensor may be arranged at Position B.

Also, in this first embodiment, the measuring step (a) may include the following three steps: irradiating step (a-1) irradiating the first and second sensors with irradiating light; detecting step (a-2) detecting a first returning light beam that has returned from around the first sensor and a second returning light beam that has returned from around the second sensor; and calculating step (a-3) calculating the first and second concentrations based on the first and second returning light beams, respectively.

In the first embodiment, in each of the first and second sensors, a metal pattern may have been formed on their side to be irradiated with the irradiating light.

The irradiating light may be light which induces localized surface plasmon resonance in the metal pattern.

The first returning light beam may be a first surface enhanced Raman scattered light beam which has been produced in the vicinity of the metal pattern of the first sensor, and the first concentration may be calculated based on the radiant intensity of the first surface enhanced Raman scattered light beam.

Also, the second returning light beam may be a second surface enhanced Raman scattered light beam which has been produced in the vicinity of the metal pattern of the second sensor, and the second concentration may be calculated based on the radiant intensity of the second surface enhanced Raman scattered light beam.

In the first embodiment, the first and second returning light beams are surface enhanced Raman scattered light beams which have been produced by the test substance that is present in the vicinity of the metal pattern.

In the first embodiment, the first and second sensors may be embedded in the dermis of the organism.

In the first embodiment, the test substance is a substance diffusing out of the blood vessel of the organism from inside of it. In the following example, glucose is used as an exemplary test substance.

A typical exemplary method for measuring the concentration of a biogenic component according to the first embodiment and an apparatus for use in the method will now be described with reference to FIGS. 3 and 4.

In the following description, a fine particle chip 7 will be used as an example of the first sensor.

A fine particle chip 8 will be used as an example of the second sensor.

A fine particle 11 will be used as an example of the metal pattern.

Substantially parallel light beams 9 and 10 will be used as irradiating light beams.

Figure 3:
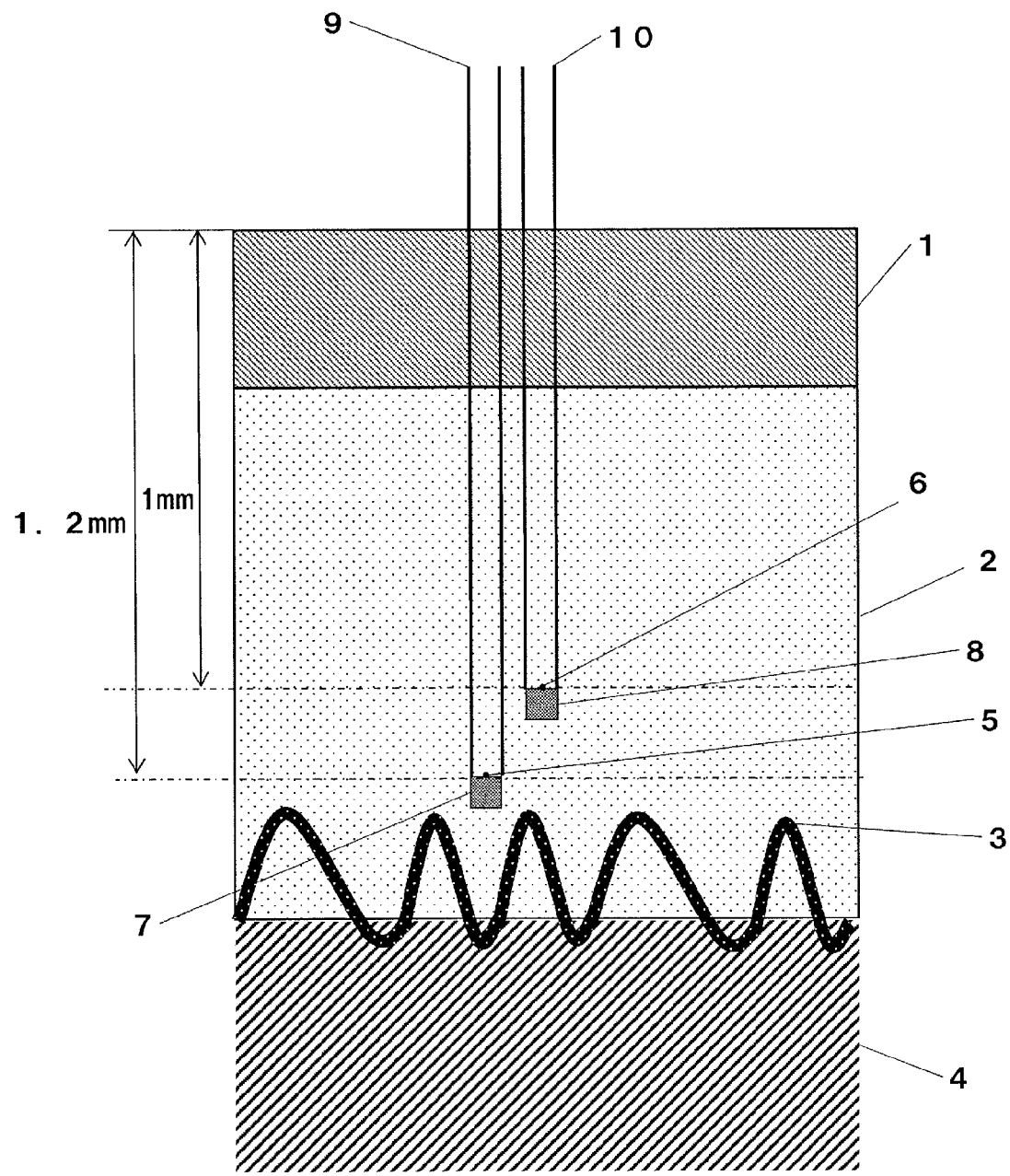
FIG. 3 is a schematic cross-sectional view of the skin irradiated with light according to a first embodiment.

FIG. 3 schematically illustrates a cross section of the skin irradiated with light. The epithelial tissue 1, dermis tissue 2, capillary blood vessels 3 and subcutaneous tissue 4 shown in FIG. 3 correspond to their counterparts shown in FIG. 1. Likewise, the dots 5 and 6 shown in FIG. 3 also respectively indicate Positions A and B in the dermis tissue 2 as in FIG. 1.

The fine particle chips 7 and 8 are arranged so that their respective upper surfaces (i.e., the surfaces closer to the body surface) are located at Position A and B, respectively, in the dermis tissue 2. The fine particle chips 7 and 8 are kept immersed in interstitial fluid which is a body fluid between tissue cells of the dermis tissue 2.

Figure 4:
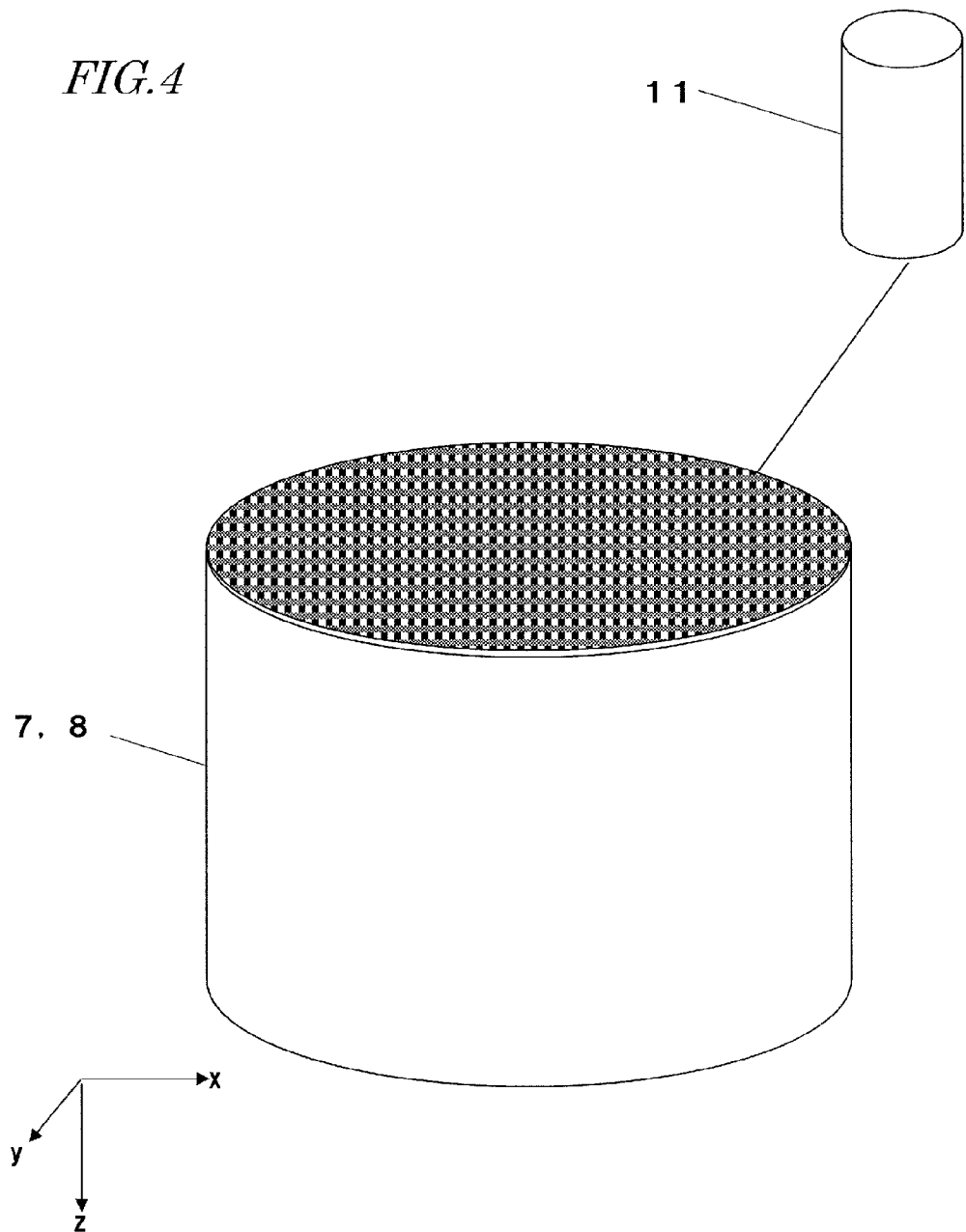
FIG. 4 illustrates an exemplary fine particle chip 7, 8 according to the first embodiment.

FIG. 4 illustrates an exemplary fine particle chip 7, 8, which includes a substrate and fine particles 11 arranged on the surface of the substrate. When irradiated with light, the fine particles 11 induce localized surface plasmon resonance. The fine particles 11 may be nanoparticles. The fine particles 11 may be gold nano-rods having a diameter of approximately 10 nm and a length of approximately 38 nm. The absorption spectrum of the fine particles 11 has a peak of absorption at a wavelength of 785 nm and a half width at half maximum of approximately 70 nm. In this description, the wavelength at the peak of absorption will be hereinafter referred to as a "localized surface plasmon resonance wavelength". Also, these fine particle chips 7 and 8 have the same shape and the same property.

The substrate may have a diameter of approximately 100 µm and a thickness of approximately 100 µm. Examples of materials for the substrate include resin materials such as an acrylic resin, glass and silicon. The fine particles 11 may be gold nano-rods. The fine particles 11 are arranged so that their major axis direction becomes parallel to the xy plane shown in FIG. 4 (i.e., parallel to the upper surface of the substrate). In other words, the major axis is parallel to the xy plane and the lateral surface of the fine particles 11 is in contact with the upper surface of the substrate. It should be noted that the y direction is a direction which intersects at right angles with the x direction on the surface of the substrate and the z direction is parallel to the thickness direction of the substrate.

As shown in FIG. 3, the fine particle chips 7 and 8 are embedded in the dermis tissue 2 so that their upper surface with the fine particles 11 is parallel to the surface of the epithelial tissue 1. The distance from the top surface of the epithelial tissue 1 to the upper surface of the fine particle chip 7 (i.e., the position where the fine particles 11 are arranged) is approximately 1.2 mm. The distance from the top surface of the epithelial tissue 1 to the upper surface of the fine particle chip 8 (i.e., the position where the fine particles 11 are arranged) is approximately 1.0 mm.

The substantially parallel light beams 9 and 10 shown in FIG. 3 have a wavelength of 785 nm, and have a circular beam cross section having a diameter of 100 µm. The substantially parallel light beams 9 and 10 are transmitted through the epithelial tissue 1, propagate through the dermis tissue 2 and then irradiate the fine particles 7 and 8, respectively. The substantially parallel light beams 9 and 10 propagate in the z direction shown in FIG. 3. When the substantially parallel light beams 9 and 10 irradiate the fine particle chips 7 and 8, respectively, the fine particles 11 induce localized surface plasmon resonance to enhance the strength of the electromagnetic field in the vicinity of the fine particles 11. As a result, the Raman scattered light of the substance which is present in the vicinity of (within a distance of 0.5 to 30 nm from) the fine particles 11 is enhanced. In this manner, surface enhanced Raman scattered light is produced.

The surface enhanced Raman scattered light has a radiant intensity that is at least $10^5$ times as high as that of ordinary Raman scattered light. That is why the surface enhanced Raman scattered light produced from the substance in the vicinity of the fine particles 11 has a far higher radiant intensity than Raman scattered light which is produced at the surface of the skin (i.e., at the horny layer of the epithelial tissue 1), in the epithelial tissue 1 or in the dermis tissue 2. This means that only the Raman scattered light of the substance that is located in the vicinity of the fine particles 11 has been enhanced selectively.

Figure 5:
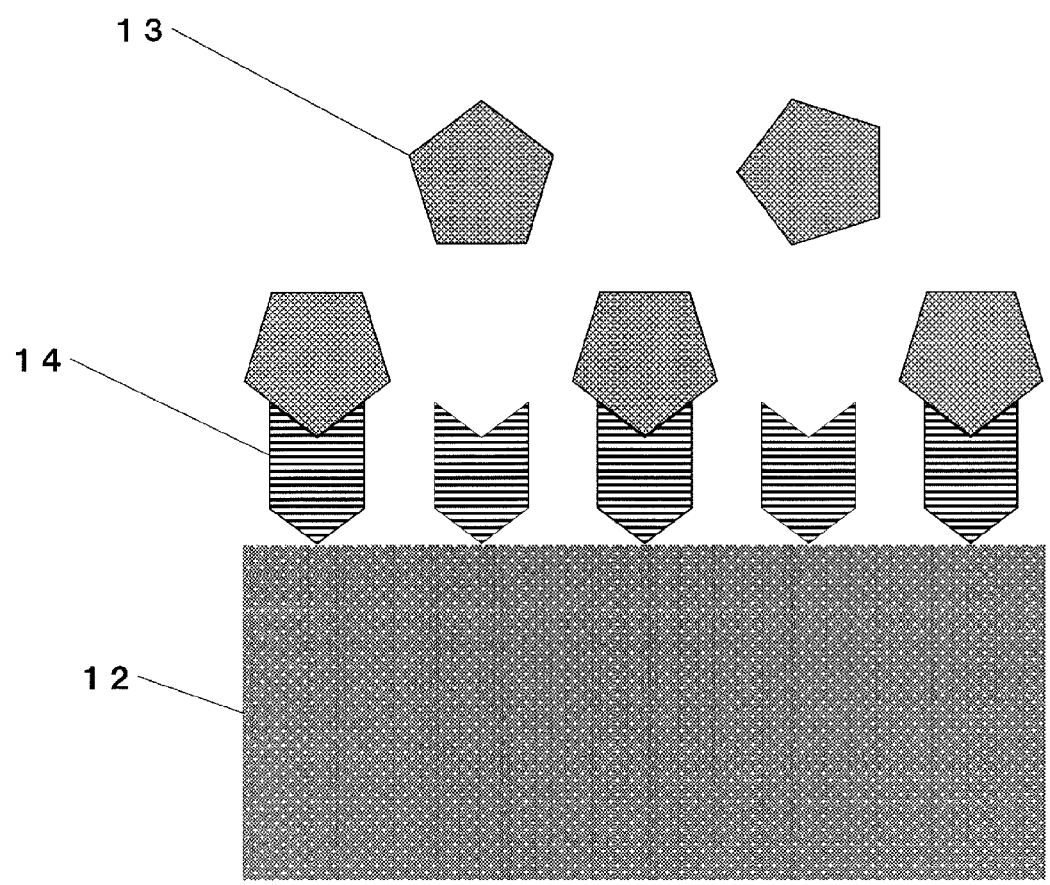
FIG. 5 schematically illustrates a trapping substance immobilized on fine particles and a test substance according to the first embodiment.

In the exemplary configuration shown in FIG. 5, a trapping substance 14 to trap a test substance 13 such as glucose specifically is immobilized on a gold surface portion 12 of the fine particles 11. If the test substance is glucose, examples of this trapping substance 14 include boronic acid compounds having a mercapto group such as 4-MPBA (4-mercaptophenylboronic acid, $C_6H_7BO_2S$) and 3-MPBA (3-mercaptophenylboronic acid, $C_6H_7BO_2S$). Such a boronic acid compound having a mercapto group can be immobilized by bonding the mercapto group to the gold surface of the fine particles 11. Furthermore, by bonding a boronic acid group to glucose specifically, glucose can be trapped specifically.

The trapping substance 14 may also be 1-mercaptoundeca-tri-ethylene glycol $(HS(CH_2)_{11}(OCH_2CH_2)_3OH)$ or mercaptohexanol $(HS(CH_2)_6OH)$. Such a trapping substance can also be immobilized by bonding the mercapto group to the gold surface of the fine particles 11. Furthermore, by making glucose enter the gap between these adjacent molecules, glucose can be trapped.

Since the trapping substance 14 is located in the vicinity of the fine particles 11, the Raman scattered light of the trapping substance 14 is enhanced to produce surface enhanced Raman scattered light. Likewise, since the test substance 13 trapped by the trapping substance 14 is also located in the vicinity of the fine particles 11, the Raman scattered light of the test substance 13 is enhanced to produce surface enhanced Raman scattered light.

The radiant intensity of the surface enhanced Raman scattered light of the test substance 13 is proportional to the quantity of the test substance 13 trapped by the trapping substance 14. Also, the quantity of the test substance 13 trapped by the trapping substance 14 increases as the concentration of the test substance 13 in the interstitial fluid rises. That is to say, the quantity of the test substance 13 trapped by the trapping substance 14 depends on the concentration of the test substance 13. That is why the radiant intensity of the surface enhanced Raman scattered light of the test substance 13 depends on the concentration of the test substance 13. Consequently, by measuring the radiant intensity of the surface enhanced Raman scattered light of the test substance 13, the concentration of the test substance 13 is calculable.

As can be seen from the foregoing description, the concentration of the test substance 13 around the fine particles 11 of the fine particle chip 7, 8 is calculable based on the surface enhanced Raman scattered light of the test substance 13 that has been produced in the region around the fine particles 11 of the fine particle chip 7, 8.

In this case, if the test substance 13 is glucose, the regions around the fine particles 11 in the fine particle chips 7 and 8 correspond to Positions A and B, respectively. That is why the concentrations of glucose at these positions in the interstitial fluid are measurable individually.

Figure 6:
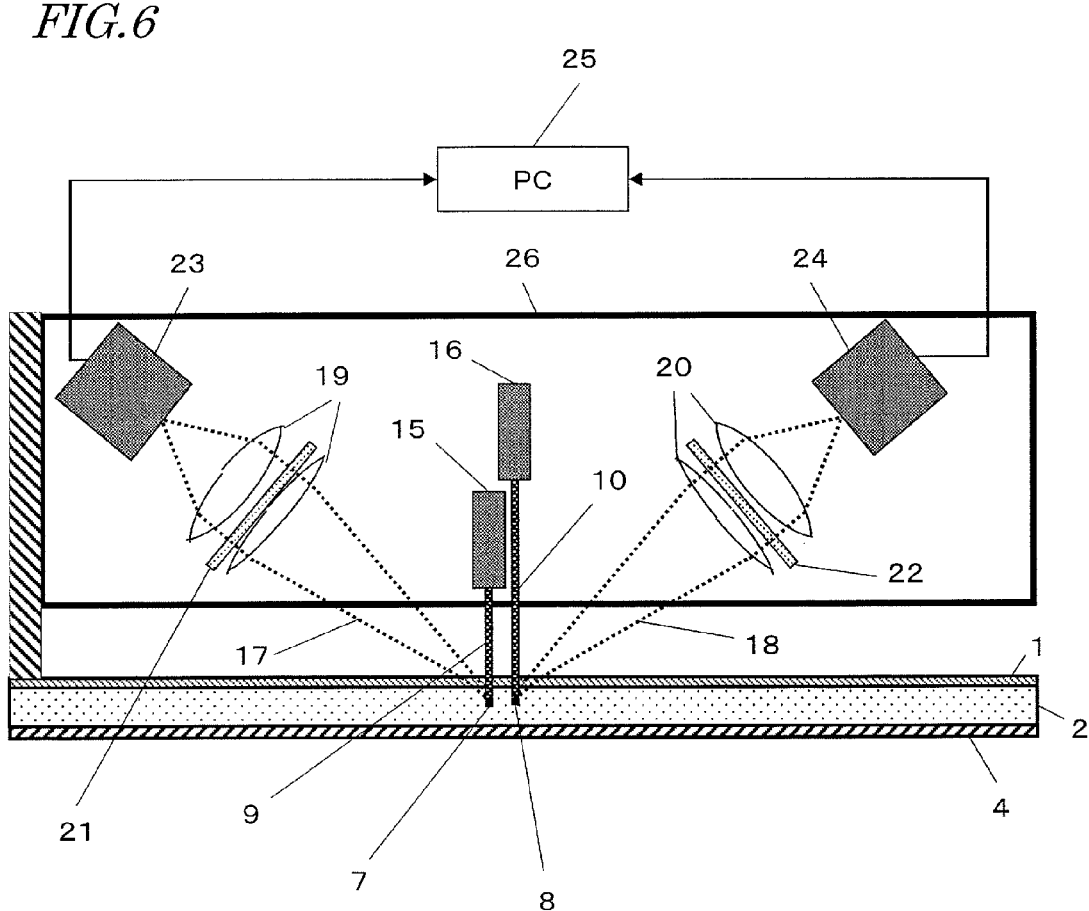
FIG. 6 illustrates an exemplary measuring apparatus according to the first embodiment.

Next, an exemplary apparatus having the ability to measure the concentrations of glucose at those Positions A and B in the interstitial fluid individually will be described with reference to FIG. 6. In FIG. 6, the epithelial tissue 1, dermis tissue 2, subcutaneous tissue 4, fine particle chips 7, 8 and substantially parallel light beams 9, 10 correspond to their counterparts identified by the same reference numerals in FIGS. 1 to 5.

Each of light sources 15 and 16 is a module in which a semiconductor laser diode and an irradiation optical system are assembled together. The light sources 15 and 16 produce substantially parallel light beams 9 and 10, respectively. Both of the substantially parallel light beams 9 and 10 have a wavelength of 785 nm and a radiant intensity of 2 mW, and have a circular beam cross section with a diameter of 100 μm. The substantially parallel light beams 9 and 10 respectively irradiate the fine particle chips 7 and 8 in the dermis tissue 2. The fine particle chips 7 and 8 are arranged so as to be spaced apart from each other by at least 300 μm along the surface of the skin. That is why the fine particle chip 7 is not irradiated with the substantially parallel light beam 10, and the fine particle chip 8 is not irradiated with the substantially parallel light beam 9, either.

The surface enhanced Raman scattered light 17 produced on the fine particle chip 7 is transmitted through an optical system 19 and converged on an optical sensor 23. The optical system 19 may include a group of lenses. A spectral filter 21 transmits only light of a particular wavelength. The transmission wavelength of the spectral filter 21 is set to be as long as the wavelength of the Raman scattered light of the test substance 13. In the same way, the surface enhanced Raman scattered light 18 produced on the fine particle chip 8 is transmitted through an optical system 20 and converged on an optical sensor 24. The optical system 20 may include a group of lenses. A spectral filter 22 transmits only light with a particular wavelength. The transmission wavelength of the spectral filter 22 is set to be as long as the wavelength of the Raman scattered light of the test substance 13. In this case, the optical system 19 is arranged so that the surface enhanced Raman scattered light produced on the fine particle chip 8 is not incident on the optical sensor 23. Likewise, the optical system 20 is arranged so that the surface enhanced Raman scattered light produced on the fine particle chip 7 is not incident on the optical sensor 24.

A computer (PC) 25 calculates individually the concentrations of glucose at Positions A and B in the interstitial fluid based on the respective output signals of the optical sensors 23 and 24. In addition, the computer 25 may have at least one of the functions of: providing a blood glucose level after having checked out the validity of the measured value; providing a provisional blood glucose level; and providing information about a steep change in blood glucose level as will be described later.

A supporting member 26 holds the light sources 15, 16, optical systems 19, 20, spectral filters 21, 22, and optical sensors 23, 24.

By adopting such a configuration, the concentrations of glucose at Positions A and B in the interstitial fluid are measurable.

If the difference in glucose concentration between those Positions A and B in the interstitial fluid is less than a predetermined value (e.g., if these two concentrations are equal to each other), decision may be made that no spatial glucose concentration gradient has been produced in the interstitial fluid. In that case, decision may be made that the equilibrium has already been established between the blood glucose level in the capillary blood vessels 3 and the concentration of glucose in the interstitial fluid.

On the other hand, if the difference in glucose concentration between those Positions A and B in the interstitial fluid is equal to or greater than the predetermined value, decision may be made that a spatial glucose concentration gradient has been produced in the interstitial fluid. In that case, decision may be made that the equilibrium has not been established yet between the blood glucose level in the capillary blood vessels 3 and the concentration of glucose in the interstitial fluid.

In this case, to see if the glucose concentrations are substantially equal to each other, the difference in glucose concentration between those Positions A and B in the interstitial fluid may be calculated, and decision may be made whether the difference is less than the predetermined value or not. If the answer is YES, those concentrations may be regarded as substantially equal to each other.

The predetermined value may be set to be approximately equal to the required quantitative accuracy of the blood glucose level. For example, if the required quantitative accuracy of the blood glucose level is ±7.5 [mg/dl], then the predetermined value may also be set to be 7.5 [mg/dl].

According to this embodiment, the concentrations of glucose at those Positions A and B in the interstitial fluid are measurable in this manner. And decision may be made, based on the difference between these two concentrations, whether or not an equilibrium has been established yet between the blood glucose level in the capillary blood vessels 3 and the concentration of glucose in the interstitial fluid.

As can be seen from the foregoing description, according to this first embodiment, the decision step (b) may be the step of deciding, if the difference between first and second concentrations is equal to or greater than a predetermined value, that the equilibrium has not been established yet between a concentration of a test substance in a blood vessel and a concentration of the test substance measured at a position inside of an organism but outside of the blood vessel of the organism.

Also, according to this first embodiment, the decision step (b) may be the step of deciding, if the difference between first and second concentrations is less than a predetermined value, that the equilibrium has already been established between a concentration of a test substance in a blood vessel and a concentration of the test substance measured at a position inside of an organism but outside of the blood vessel of the organism.

Optionally, if decision has been made in the decision step (b) that the equilibrium has already been established, either the measured value of the first concentration or that of the second concentration may be output as the concentration of the test substance in the organism.

In this case, if decision has been made in the decision step (b) that the equilibrium has already been established, the measured value of the first concentration may be output as the concentration of the test substance in the organism.

As a result, a measured value that is closer to the concentration of the test substance in the blood vessel may be output.

This decision result may be used in the following manner.

For example, if decision has been made that the equilibrium has not been established yet (i.e., if the difference in glucose concentration between Positions A and B in the interstitial fluid is equal to or greater than a predetermined value), the apparatus may enter a standby mode. And when decision is made that the equilibrium has been established, the apparatus may output a measured value of the glucose concentration.

The measured value may be transmitted to a device of a higher level or a memory. The measured value may be presented by a display so that the user of this measuring apparatus may check out the result of measurement.

In this manner, if the blood glucose level is not provided until it is confirmed that the equilibrium has been established, it is possible to avoid a measured value having error caused by a time lag between rises in blood glucose level and the concentration of glucose in the interstitial fluid. In other words, if the equilibrium has been established, the measured value may be regarded as a valid one. By judging its validity in this manner, the degree of reliability of the measured value is increased.

On the other hand, if the blood glucose level is changing steeply now and the equilibrium has not been established yet, the glucose concentration at Position A, which is a measured value that starts to change earlier than the glucose concentration at Position B, may be output as a provisional value and a signal indicating that the measured value is a provisional one may be output at the same time.

This provisional value is closer to the blood glucose level in the capillary blood vessels 3, and therefore, has less significant error. By outputting this provisional value, a provisional blood glucose level can be detected even while the blood glucose level is changing steeply in the capillary blood vessels 3. In this case, since a signal indicating that this is a provisional value is also output at the same time, information about a steep change in blood glucose level is provided, thus achieving advantageous clinical effects.

As can be seen from the foregoing description, according to this first embodiment, if decision has been made in the decision step (b) that the equilibrium has not been established yet, notification may be made that the concentration of the test substance in the blood vessel is now changing steeply.

Also, according to this first embodiment, if decision has been made in the decision step (b) that the equilibrium has not been established yet, a measured value of the first concentration may be output provisionally. In that case, notification may be made that the measured value of the first concentration output is a provisional value.

Next, the characteristics of the spectral filters 21 and 22 will be described.

If the test substance 13 is glucose and if Raman scattered light produced by glucose is going to be detected by the optical sensors 23 and 24, the transmission wavelength of the spectral filters 21 and 22 is tuned to the wavelength of the Raman scattered light produced by glucose. In that case, the output signals of the optical sensors 23 and 24 change proportionally to the number of glucose molecules trapped by the trapping substance 14. FIG. 1 of Melissa F. Mrozek and Michael J. Weaver, "Detection and Identification of Aqueous Saccharides by Using Surface-Enhanced Raman Spectroscopy", Analytical Chemistry, Vol. 74, No. 16, 4069-4075, 2002 (which will be hereinafter referred to as "Non-Patent Document 1") shows the surface enhanced Raman scattering spectrum of glucose. As shown in FIG. 1 of Non-Patent Document 1, the surface enhanced Raman scattering spectrum of glucose has a plurality of peaks unique to glucose in the Raman shift range of 300 $cm^{-1}$ to 1500 $cm^{-1}$.

Among those peaks, a peak at a Raman shift of 1120 $cm^{-1}$ does not agree with a peak of the Raman scattering spectrum of albumin or creatinine. That is to say, that is a peak unique to glucose. For that reason, the radiant intensity of the surface enhanced Raman scattered light at the Raman shift of 1120 cm$^{-1}$ is proportional to only the concentration of glucose.

If the wavelength of the light emitted from the light source 15, 16 is 785 nm, then a spectral filter 21, 22, of which the transmission wavelength is shorter than 785 nm by a wave number of 1120 cm$^{-1}$ (i.e., wavelength λ=860.7 nm), is adopted.

The relation between the wavelength λ and the wave number k is represented by the following Equation (1):

$$k(\text{cm}^{-1})=10^{7}/\lambda(\text{nm}) \quad (1)$$

A wavelength λ of 785 nm is converted into a wave number k of 12739 cm$^{-1}$. The wave number of the peak unique to glucose is smaller than 12739 cm$^{-1}$ by 1120 cm$^{-1}$. Therefore, the wave number is 12739 (cm$^{-1}$)−1120 (cm$^{-1}$)=11619 (cm$^{-1}$). 11619 cm$^{-1}$ is converted into a wavelength of 860.7 nm.

Next, it will be described with reference to FIGS. 7 and 8 how the concentrations of glucose at Positions A and B in the interstitial fluid may be calculated individually based on the output signals of the optical sensors 23 and 24.

Figure 7:
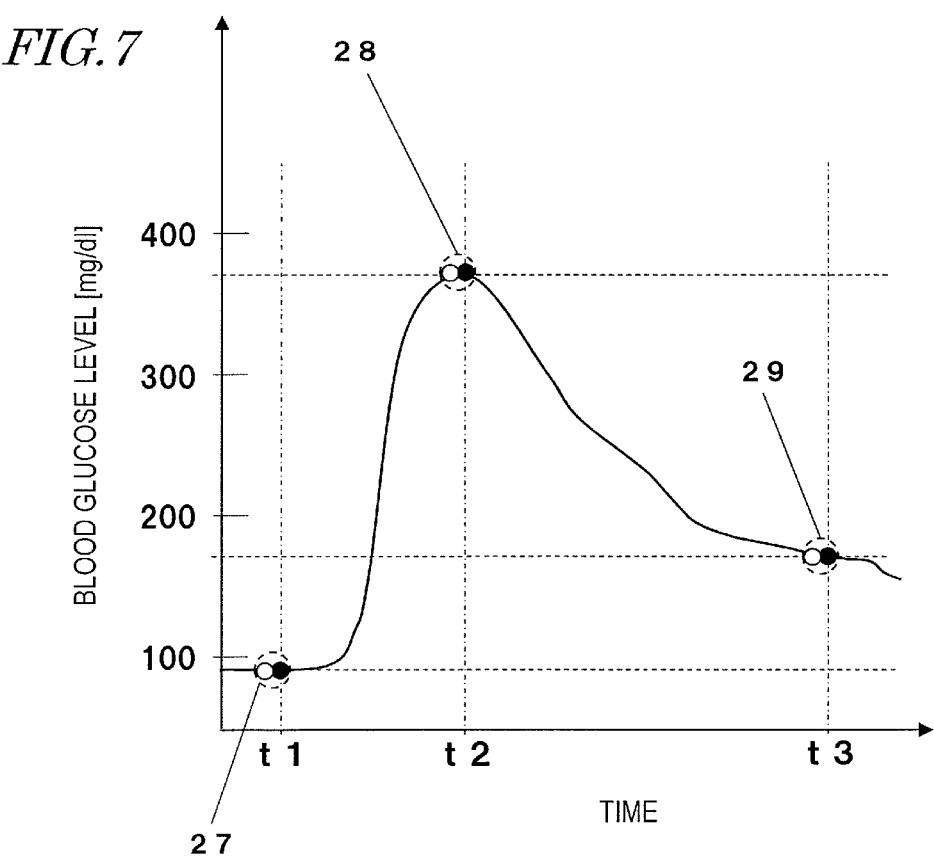
FIG. 7 is a graph showing an exemplary process of plotting calibration curves according to the first embodiment.

FIG. 7 shows how the concentration of glucose in a diabetic's blood (i.e., his or her blood glucose level) may change with time. In FIG. 7, the abscissa indicates the time and the ordinate indicates the blood glucose level. First of all, the blood glucose level when he or she is hungry is measured. In this case, the blood sample collected is subjected to measurement using an ordinary blood glucose meter. It should be noted that multiple blood samples are collected and subjected to measurements using a blood glucose meter. In this manner, the operator can confirm that his or her blood glucose level is stabilized, and the respective output signals of the optical sensors 23 and 24 are measured and recorded using the measuring apparatus of this first embodiment. In FIG. 7, the blood glucose levels measured this time by an ordinary blood glucose meter are indicated by open and solid circles ○ and ● in the dotted circle 27. Specifically, the open circle ○ indicates the blood glucose level measured for the first time and the solid circle ● indicates the blood glucose level measured for the second time. In this manner, confirmation is made that the blood glucose levels measured for the first and second times are both 90 mg/dl. And when the blood glucose level is gotten for the second time (indicated by the solid circle ● in FIG. 7), the respective output signals of the optical sensors 23 and 24 are measured. After that, glucose of 75 g is taken at a point in time t1.

One hour later, measurements are carried out a number of times using an ordinary blood glucose meter again to confirm that his or her blood glucose level is stabilized, and the respective output signals of the optical sensors 23 and 24 are measured and recorded using the measuring apparatus of this first embodiment. In FIG. 7, the blood glucose levels measured this time are indicated by open and solid circles ○ and ● in the dotted circle 28. Specifically, the open circle ○ indicates the blood glucose level measured for the first time and the solid circle ● indicates the blood glucose level measured for the second time. In this manner, confirmation is made that the blood glucose levels measured for the first and second times are both 370 mg/dl. And when the blood glucose level is gotten for the second time (indicated by the solid circle ● in FIG. 7), the respective output signals of the optical sensors 23 and 24 are measured and recorded at a point in time t2.

Next, two hours later than t2, measurements are carried out a number of times using an ordinary blood glucose meter again to confirm that his or her blood glucose level is stabilized, and the respective output signals of the optical sensors 23 and 24 are measured using the measuring apparatus of this first embodiment. In FIG. 7, the blood glucose levels measured this time are indicated by open and solid circles ○ and ● in the dotted circle 29. Specifically, the open circle ○ indicates the blood glucose level measured for the first time and the solid circle ● indicates the blood glucose level measured for the second time. In this manner, confirmation is made that the blood glucose levels measured for the first and second times are both 170 mg/dl. And when the blood glucose level is gotten for the second time (indicated by the solid circle ● in FIG. 7), the respective output signals of the optical sensors 23 and 24 are measured and recorded at a point in time t3.

Figure 8:
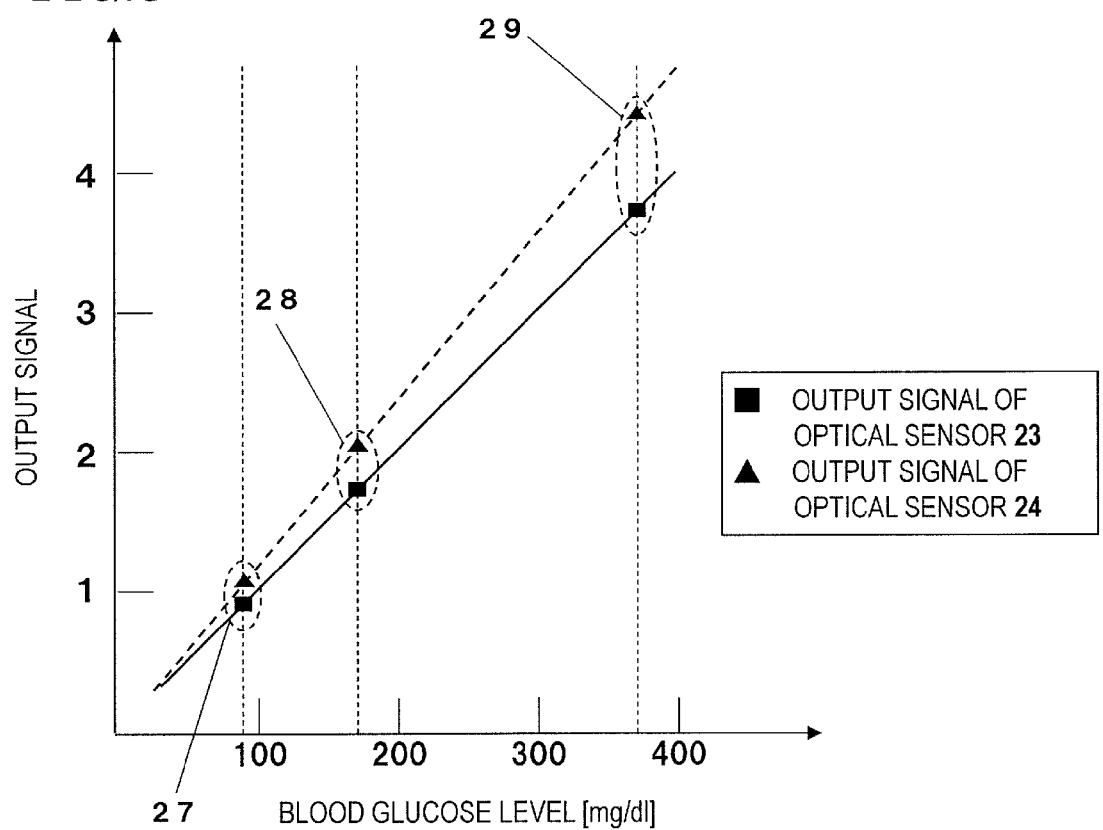
FIG. 8 is a graph showing an exemplary process of plotting calibration curves according to the first embodiment.

FIG. 8 shows how the respective output signals of the optical sensors 23 and 24 change with the blood glucose levels as indicated by the solid circles ● in FIG. 7. In FIG. 8, the abscissa indicates the blood glucose level and the ordinate indicates the output signal (signal intensity). Specifically, the solid square ■ indicates the output signal of the optical sensor 23 and the solid triangle ▲ indicates the output signal of the optical sensor 24.

A linear line which is most approximate to the line graph that connects together the output signal values of the optical sensor 23 (as indicated by the solid squares ■ in FIG. 8) is calculated and indicated by the solid line. On the other hand, a linear line which is most approximate to the line graph that connects together the output signal values of the optical sensor 24 (as indicated by the solid triangles ▲ in FIG. 8) is calculated and indicated by the dotted line. Using these solid and dotted lines as calibration curves, blood glucose levels are calculated based on the respective output signals of the optical sensors 23 and 24.

In this example, each calibration curve is supposed to be plotted based on the data about three different output signal values of the optical sensor 23, 24. Naturally, however, this is only an example, and the number of the output signal values to use does not have to be three. Rather as long as there are at least two output signal values available, a calibration curve can be plotted.

Typically, to confirm that the blood glucose level is stabilized, blood samples are collected at least twice and blood glucose levels are measured by an ordinary blood glucose meter. Unless the results of the two measurements reveal that the blood glucose level is stabilized, blood glucose levels are measured at least two more times after the standby and then the degree of stability is checked out. By repeatedly performing this operation over and over again until the blood glucose level turns to be sufficiently stabilized, the calibration curves shown in FIG. 8 are obtained.

It should be noted that each individual person's skin has a different light propagation property from any other person's. For that reason, it is advantageous to plot respective calibration curves on a person-by-person basis. On top of that, if the fine particle chip 7, 8 is embedded at a different position in the skin, then the resultant light propagation property will also vary. That is why every time the fine particle chip 7, 8 is embedded in the skin, a calibration curve may be plotted. In this manner, by plotting a calibration curve every time the condition changes, further improvement of the accuracy of measurement is achieved.

As can be seen from the foregoing description, according to this embodiment, the concentrations of glucose around the fine particles 11 of the fine particle chips 7 and 8 can be calculated based on the output signals of the optical sensors 23 and 24. As a result, the concentrations of glucose at Positions A and B in the interstitial fluid are measurable individually. Also, if the difference in glucose concentration between those Positions A and B in the interstitial fluid is less than a predetermined value (e.g., if these two concentrations are equal to each other), decision may be made that the equilibrium has already been established between the blood glucose level in the capillary blood vessels 3 and the concentration of glucose in the interstitial fluid. And if the validity of the measurements is confirmed and data about blood glucose levels, for example, is provided on sensing that the equilibrium has been established, the degree of reliability of the measured values is increased.

On the other hand, if the blood glucose level is still changing steeply and the equilibrium has not been established yet, information about such a steep change in blood glucose level may be provided and advantageous clinical effects are achieved.

Embodiment 2

A method for measuring the concentration of a biogenic component and an apparatus for use to carry out such a method according to a second embodiment will now be described.

In this embodiment, the concentration of a test substance 13 is measured based on the Raman scattered light of a trapping substance 14.

According to this second embodiment, a trapping substance to trap the test substance may be immobilized on the metal patterns of first and second sensors.

According to this second embodiment, first and second returning light beams may be surface enhanced Raman scattered light beams which have been produced by the trapping substance which is present in the vicinity of the metal patterns.

The measuring apparatus may have the same configuration as what has already been described for the first embodiment with reference to FIG. 6. Nevertheless, in this embodiment, the transmission wavelength range of the spectral filters 21 and 22 is tuned to the wavelength of the Raman scattered light produced by the trapping substance 14.

In FIG. 5, when the trapping substance 14 bonds itself to the test substance 13, the radiant intensity of the surface enhanced Raman scattered light produced by the trapping substance 14 varies. The magnitude of this variation is proportional to the number of molecules of the trapping substance 14 bonded to the test substance 13. The number of molecules of the trapping substance 14 bonded to the test substance 13 increases as the concentration of the test substance 13 in the interstitial fluid rises. That is to say, the number of molecules of the trapping substance 14 bonded to the test substance 13 depends on the concentration of the test substance 13. Consequently, the variation in the radiant intensity of the surface enhanced Raman scattered light produced by the trapping substance 14 depends on the concentration of the test substance 13. That is why by measuring the variation in the radiant intensity of the surface enhanced Raman scattered light produced by the trapping substance 14, the concentration of the test substance 13 is calculable.

In the example to be described below, the test substance 13 is supposed to be glucose and the trapping substance 14 is supposed to be 4-MPBA.

If the test substance 13 is glucose and if the trapping substance 14 is 4-MPBA, the glucose concentrations are measurable by making the optical sensors 23 and 24 detect the Raman scattered light produced by 4-MPBA. In that case, the transmission wavelength of the spectral filters 21 and 22 is tuned to the wavelength of the Raman scattered light produced by 4-MPBA.

Figure 9:
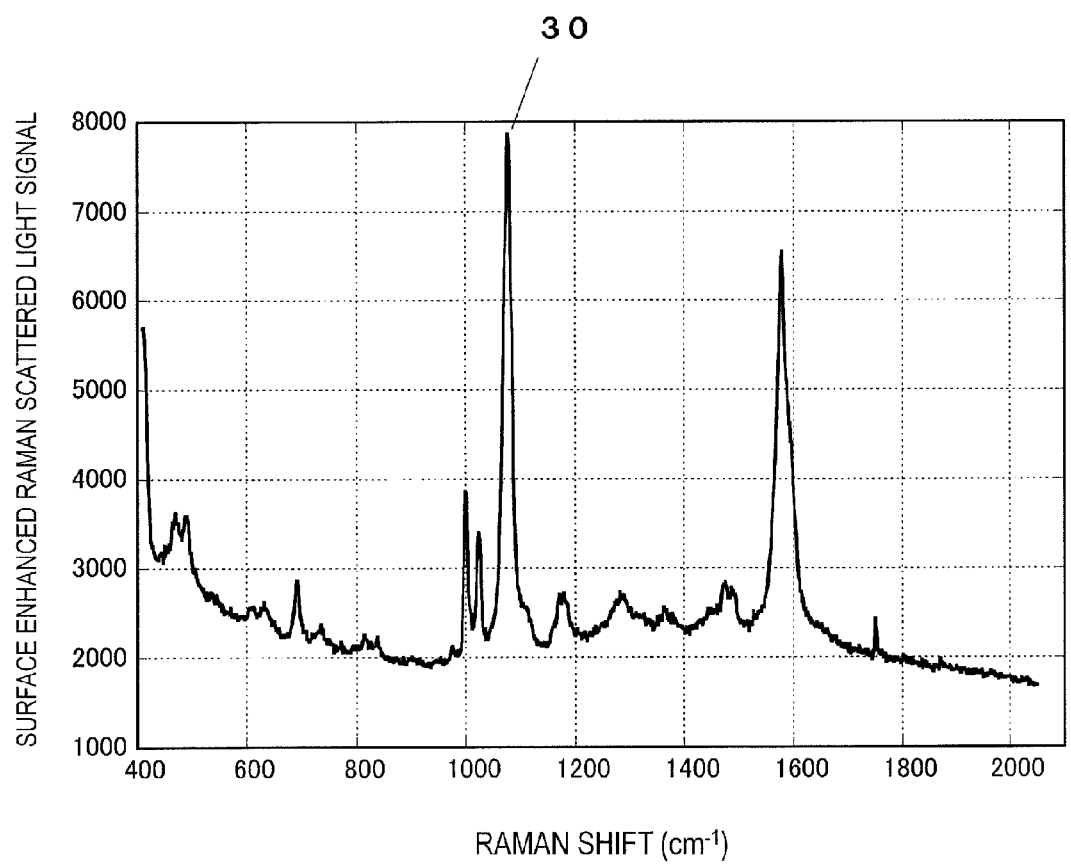
FIG. 9 is a graph showing an exemplary surface enhanced Raman scattering spectrum of a trapping substance according to a second embodiment.

FIG. 9 shows the Raman scattering spectrum of 4-MPBA in the range of Raman shift between 400 $cm^{-1}$ and 2000 $cm^{-1}$.

Among the multiple peaks shown in FIG. 9, a peak 30 at a Raman shift of 1075 $cm^{-1}$ does not agree with a peak of the Raman scattering spectrum of albumin or creatinine. In addition, this peak 30 becomes even higher as 4-MPBA gets bonded to glucose. The magnitude of increase in the height of the peak 30 is proportional to the number of 4-MPBA molecules bonded to glucose, which increases as the concentration of glucose in the interstitial fluid rises. That is to say, the number of 4-MPBA molecules bonded to glucose depends on the concentration of glucose. Consequently, the magnitude of increase in the height of the peak 30 representing the surface enhanced Raman scattered light produced by 4-MPBA depends on the concentration of glucose. The magnitude of increase in the height of the peak 30 corresponds to the magnitude of increase in the level of the output signals of the optical sensors 23, 24. That is why the concentration of glucose is calculable based on the output signals of the optical sensors 23 and 24. It should be noted that among major substances in the interstitial fluid, 4-MPBA will get bonded to only glucose, and therefore, the concentration of glucose is measurable specifically.

If the wavelength of the light emitted from the light source 15, 16 is 785 nm, then a spectral filter 21, 22, of which the transmission wavelength is shorter than 785 nm by a wave number of 1075 $cm^{-1}$ (i.e., wavelength $\lambda$=857.3 nm), is adopted. The relation between the wavelength $\lambda$ and the wave number k is just as represented by Equation (1). A wavelength $\lambda$ of 785 nm is converted into a wave number k of 12739 $cm^{-1}$. The wave number of the peak unique to 4-MPBA is smaller than 12739 $cm^{-1}$ by 1075 $cm^{-1}$. Therefore, the wave number is 12739 ($cm^{-1}$)−1075 ($cm^{-1}$)=11664 ($cm^{-1}$). 11664 $cm^{-1}$ is converted into a wavelength of 857.3 nm.

Next, the concentrations of glucose at Positions A and B in the interstitial fluid are calculated individually based on the output signals of the optical sensors 23 and 24. In this embodiment, the degree of stability of the blood glucose level may be checked out and the output signals of the optical sensors 23 and 24 may be measured in the same way as in the first embodiment to obtain a graph similar to the one shown in FIG. 7. Subsequently, a graph similar to the one shown in FIG. 8 is drawn up to plot calibration curves. And by using these calibration curves, the concentrations of glucose around the fine particles 11 of the fine particle chips 7 and 8 are calculated based on the output signals of the optical sensors 23 and 24. In this manner, the concentrations of glucose at those Positions A and B in the interstitial fluid are measurable individually.

Any metal pattern may be formed on the first and second sensors as long as the metal pattern induces localized surface plasmon resonance when irradiated with irradiating light. For example, the gold nano-rods used as the fine particles 11 in the first and second embodiments may be replaced with fine particles in which a dielectric material such as silica is coated with a metal such as gold or silver.

In the first and second embodiments, the irradiating light emitted from the light sources 15 and 16 may have a wavelength of 785 nm. As a result, the following advantages are achieved.

Generally speaking, an organism exhibits a high degree of transparency with respect to light of a wavelength of 700 nm to 900 nm. The Raman scattered light specific to glucose has a wave number which is smaller than the wave number of the irradiating light by approximately 1100 to 1200 cm$^{-1}$. That is why by setting the wavelength of the irradiating light to be within the range of 700 nm to 800 nm, both the irradiating light and the surface enhanced Raman scattered light can take advantage of that high degree of transparency.

Also, the resonance spectrum of the localized surface plasmon resonance has some breadth and a wavelength representing a peak of this resonance spectrum is generally called a "resonance wavelength". In the embodiment described above, the localized surface plasmon resonance wavelength of the fine particles 11 is supposed to agree with the wavelength of the irradiating light. However, this is only an example and these two wavelengths do not always agree with each other. Rather, the resonance wavelength and the wavelength of the irradiating light may be different from each other by approximately the half width at half maximum of the resonance spectrum of the localized surface plasmon resonance (which usually falls within a range of a few ten to a few hundred nm). Advantageously, the wavelength of the irradiating light falls within the full width at half maximum of the resonance spectrum. And such a state will be hereinafter referred to as a "state where the wavelength of the irradiating light is tuned to the localized surface plasmon resonance wavelength".

In this case, if the resonance wavelength is longer than the wavelength of the irradiating light, then a signal representing the surface enhanced Raman scattered light would be further enhanced. For that reason, the wavelength of the irradiating light may be tuned to a wavelength which is shorter than the resonance wavelength.

It should be noted that the resonance spectrum of the localized surface plasmon resonance is observable in this case as the absorption spectrum of the fine particles 11.

Embodiment 3

The following configuration will be described as an example of a third embodiment.

In this embodiment, the first sensor may be a first fluorescent fine particle, and the second sensor may be a second fluorescent fine particle.

The first and second fluorescent fine particles produce fluorescent light, of which the radiant intensity changes in reaction to the test substance in the organism, when irradiated with the irradiating light.

The irradiating light is light, of which the wavelength is tuned to the absorption wavelength of the fluorescent fine particles.

The first returning light beam is a first fluorescent light beam which has been produced in the vicinity of the first fluorescent fine particle. The first concentration is calculated based on the radiant intensity of the first fluorescent light beam.

The second returning light beam is a second fluorescent light beam which has been produced in the vicinity of the second fluorescent fine particle, and the second concentration is calculated based on the radiant intensity of the second fluorescent light beam.

Figure 10:
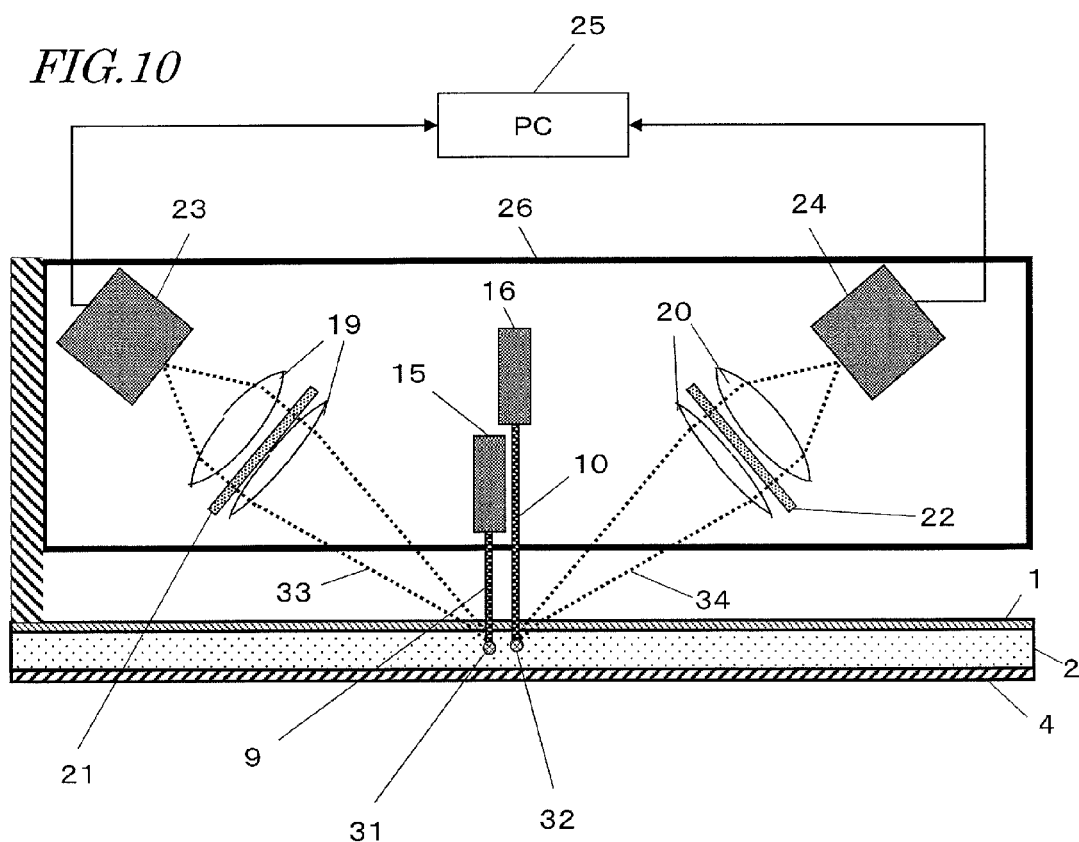
FIG. 10 illustrates an exemplary measuring apparatus according to a third embodiment.

A situation where a fluorescent fine particle is used as shown in FIG. 10 will be described in this third embodiment.

That is to say, according to this third embodiment, a fluorescent fine particle 31 is used as an example of the first fluorescent fine particle.

Also, a fluorescent fine particle 32 is used as an example of the second fluorescent fine particle.

Furthermore, a fluorescent light beam 33 is used as an example of the first fluorescent light beam.

Furthermore, a fluorescent light beam 34 is used as an example of the second fluorescent light beam.

In FIG. 10, the fluorescent fine particles 31 and 32 are exemplary spherical fine particles, of which the fluorescent light gets enhanced in reaction to glucose, and have a diameter of approximately 10 to 100 μm. When irradiated with light falling within the ultraviolet to near-infrared range of the spectrum, these fluorescent fine particles 31 and 32 absorb the irradiating light and emit fluorescent light, of which the radiant intensity is proportional to the irradiance of the irradiating light and the concentration of glucose. These fluorescent fine particles 31 and 32 are arranged at the same positions as the fine particle chips 7 and 8 shown in FIG. 6, i.e., at Positions A and B, respectively. In this embodiment, the light sources 15 and 16 irradiate the fluorescent fine particles 31 and 32 with substantially parallel light beams 9 and 10, of which the wavelength falls within the ultraviolet to near-infrared range of the spectrum. The fluorescent fine particles 31 and 32 absorb those substantially parallel light beams 9 and 10 to produce fluorescent light 33, 34. Also, the spectral filters 21 and 22 have the property to transmit light falling within the wavelength range of the fluorescent light 33, 34 thus produced. That is why the output signals of the optical sensors 23 and 24 represent the intensities of the fluorescent light 33, 34 produced by the fluorescent fine particles 31 and 32, respectively. The epithelial tissue 1, dermis tissue 2, subcutaneous tissue 4, optical systems 19, 20, computer (PC) 25, and supporting member 26 shown in FIG. 10 correspond to, and may operate in the same way as, their counterparts that have already been described for the first embodiment with reference to FIG. 6.

According to this embodiment, the concentrations of glucose at Positions A and B around the fluorescent fine particles 31 and 32 are calculable based on the output signals of the optical sensors 23 and 24 as in the first embodiment described above. As a result, the concentrations of glucose at Positions A and B in the interstitial fluid are measurable individually. Also, if the concentrations at these Positions A and B in the interstitial fluid are equal to each other, decision may be made that the equilibrium has already been established.

Typically, the concentrations of glucose at Positions A and B in the interstitial fluid are calculated individually based on the output signals of the optical sensors 23 and 24. In this embodiment, the degree of stability of the blood glucose level may be checked out and the output signals of the optical sensors 23 and 24 may be measured in the same way as in the first embodiment to obtain a graph similar to the one shown in FIG. 7. Subsequently, a graph similar to the one shown in FIG. 8 is drawn up to plot calibration curves. And by using these calibration curves, the concentrations of glucose around the fluorescent fine particles 31 and 32 are calculated based on the output signals of the optical sensors 23 and 24. In this manner, the concentrations of glucose at those Positions A and B in the interstitial fluid are measurable individually.

In this embodiment, the fluorescent light is supposed to be enhanced when reacting to glucose. However, even if fluorescent light is diminished when reacting to glucose, the concentrations of glucose at those Positions A and B in the interstitial fluid are also measurable individually by plotting the calibration curves in the same way.

The configuration of this third embodiment does not have to be combined with that of the first embodiment but may also be combined with at least one of the configuration of the first and second embodiments described above.

Embodiment 4

The following configuration will be described as an example of a fourth embodiment.

In this fourth embodiment, if decision has been made in the decision step (b) that the equilibrium has not been established yet, the region surrounding Positions A and B is heated.

Such an embodiment will now be described with reference to FIG. 11.

Figure 11:
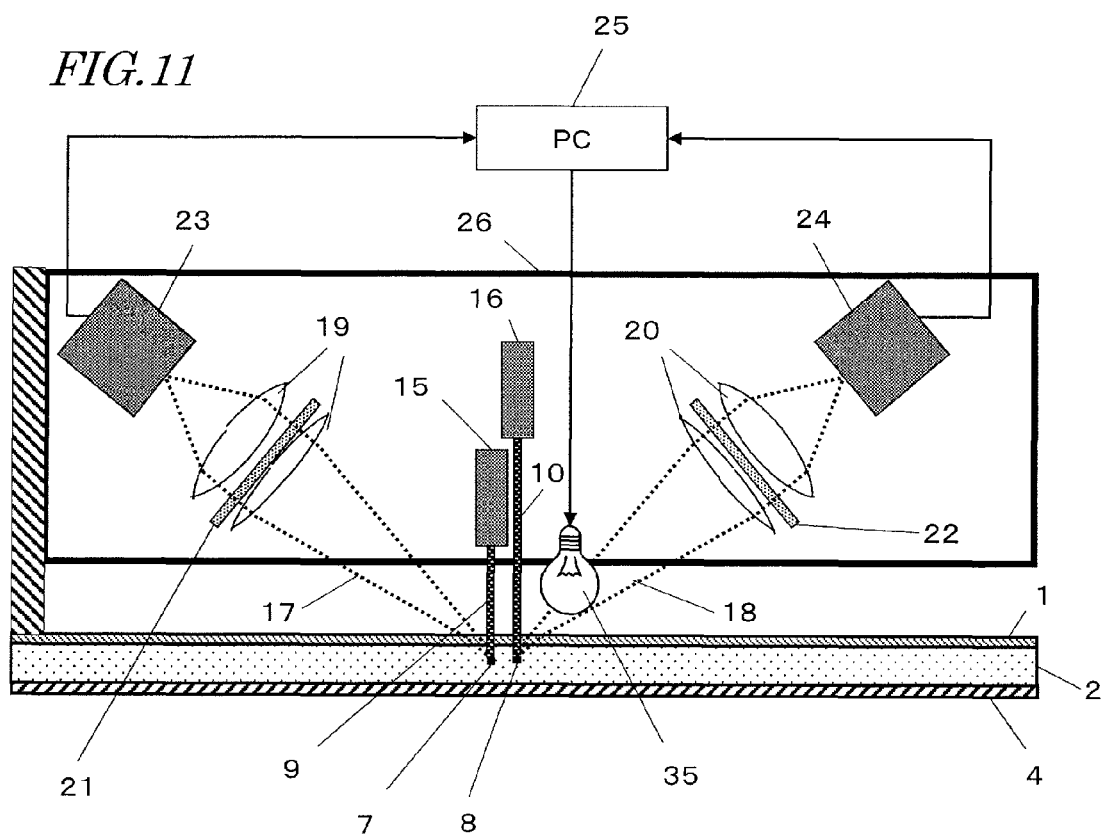
FIG. 11 illustrates an exemplary measuring apparatus according to a fourth embodiment.

In FIG. 11, a heater 35 has the function of heating the organism by irradiating the organism with an infrared ray, for example. In this embodiment, the computer (PC) 25 has the function of controlling the heater 35 and maintaining the temperature in a region surrounding the fine particle chips 7 and 8 embedded within the range of 38 to 42 degrees Celsius.

This embodiment achieves the effect of establishing an equilibrium in a shorter time between the concentrations of glucose in the interstitial fluid and the blood glucose levels by heating the organism. An example of such an operation will be described below.

As already described for the first embodiment, the difference in glucose concentration between Positions A and B in the interstitial fluid may be calculated and decision may be made that those two concentrations are substantially equal to each other if their difference is less than a predetermined value.

On the other hand, if their difference in glucose concentration is equal to or greater than the predetermined value, the computer 25 may instruct the heater 35 to heat a region surrounding the fine particle chips 7 and 8 embedded to a temperature of 38 to 42 degrees Celsius.

In this manner, an equilibrium is established in a shorter time between the glucose concentrations in the interstitial fluid and the blood glucose levels. As a result, the amount of standby time until the difference in glucose concentration becomes less than the predetermined value (i.e., until the validity of the measurement is ascertained) is also shortened.

As can be seen, according to this embodiment, a valid measured value is provided more quickly.

The configuration of this fourth embodiment does not have to be combined with that of the first embodiment but may also be combined with at least one of the configurations of the first, second, and third embodiments described above.

Embodiment 5

Figure 14:
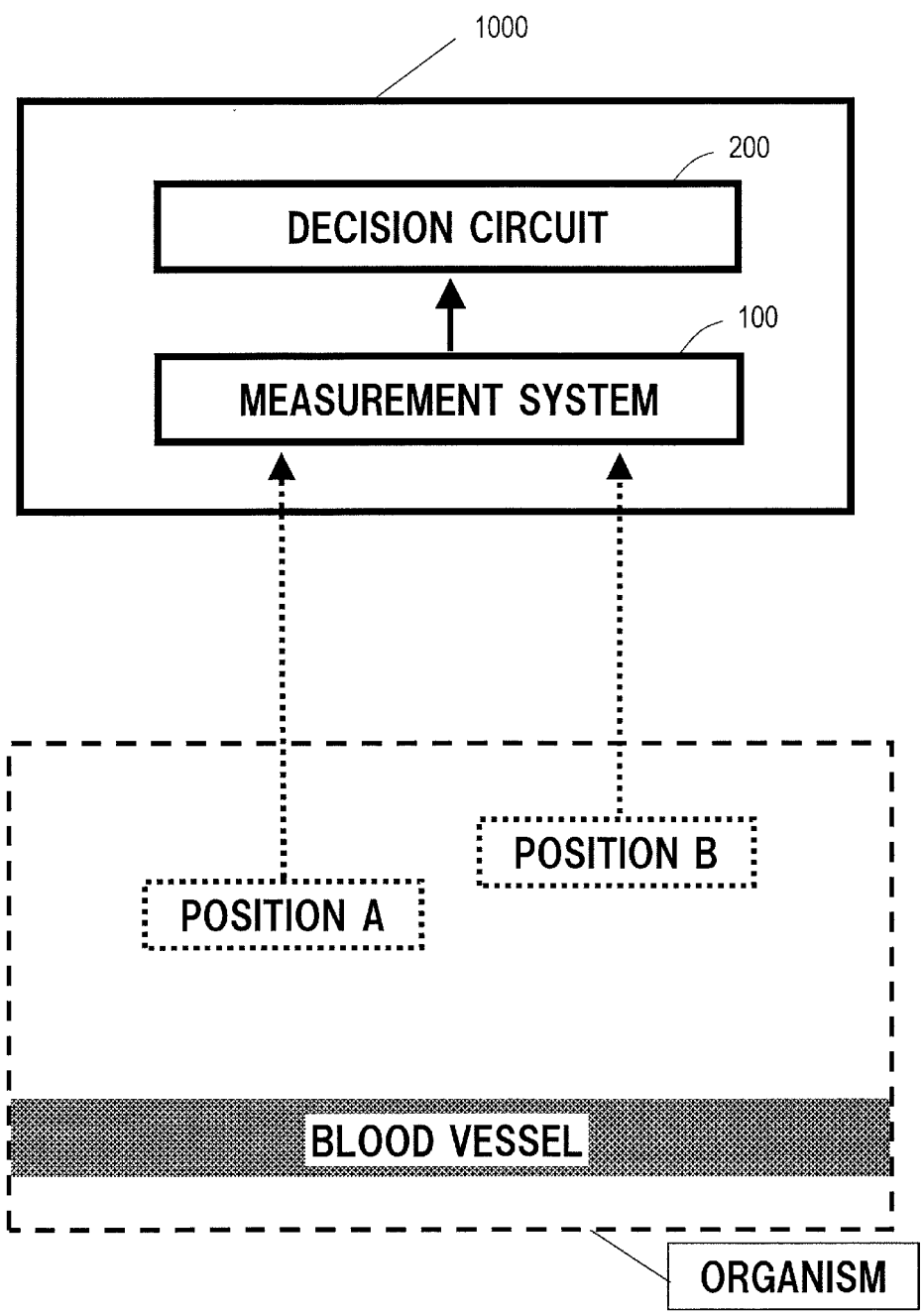
FIG. 14 illustrates an exemplary measuring apparatus according to a fifth embodiment.

FIG. 14 illustrates an exemplary configuration for a measuring apparatus according to a fifth embodiment which measures the concentration of a test substance in an organism.

The measuring apparatus 1000 shown in FIG. 14 includes a measurement system 100 (measuring means) and a decision circuit 200 (decision means).

The measurement system 100 measures first and second concentrations that are concentrations of the test substance at Positions A and B, respectively.

In this case, Positions A and B are located inside of the organism but outside of the blood vessel of the organism, and Position B is located more distant from the blood vessel than Position A is.

The decision circuit 200 determines, based on the first and second concentrations, whether or not an equilibrium has been established yet between a concentration of the test substance inside of the blood vessel and a concentration of the test substance measured at a position inside of the organism but outside of the blood vessel of the organism.

According to this configuration, decision may be made whether or not an equilibrium has been established yet between a concentration of a test substance inside of a blood vessel and a concentration of the test substance measured at a position inside of an organism but outside of the blood vessel of the organism.

As a result, if the test substance is glucose, for example, it is possible to avoid the phenomenon that the accuracy of measuring the blood glucose level decreases significantly when the blood glucose level rises steeply. Consequently, a highly reliable blood glucose measured value is provided.

Figure 15:
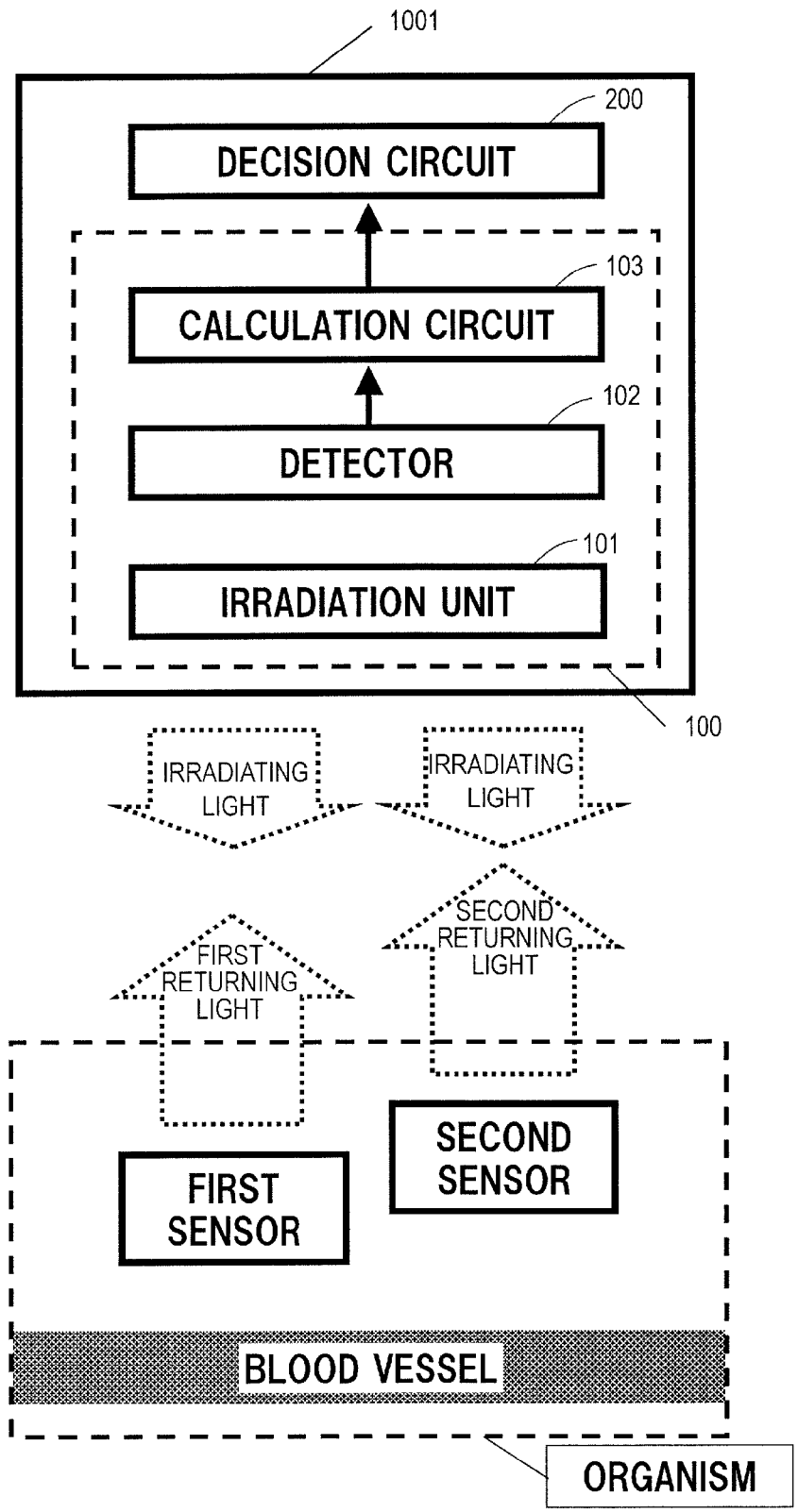
FIG. 15 illustrates another exemplary measuring apparatus according to the fifth embodiment.

It should be noted that the measurement system 100 may have any of the configurations that have already been described for the first through fourth embodiments. For example, the configuration of the measuring apparatus 1001 shown in FIG. 15 may be adopted.

According to this fifth embodiment, a first sensor may be arranged at Position A, and a second sensor may be arranged at Position B.

In this case, just like the measuring apparatus 1001, the measurement system 100 may include an irradiation unit 101, a detector 102 and a calculation circuit 103.

The irradiation unit 101 irradiates the first and second sensors with irradiating light.

The detector 102 detects a first returning light beam that has returned from around the first sensor and a second returning light beam that has returned from around the second sensor.

The calculation circuit 103 calculates the first and second concentrations based on the first and second returning light beams, respectively.

The irradiation unit 101 may have any of the configurations that have already been described for the first to fourth embodiments. For example, the irradiation unit 101 may include the light sources 15 and 16 that have been described for the first to fourth embodiments.

The detector 102 may have any of the configurations that have already been described for the first to fourth embodiments. For example, the detector 102 may include the optical sensors 23 and 24 that have been described for the first to fourth embodiments. The detector 102 may further include the optical systems 19, 20 and spectral filters 21 and 22 that have been described for the first to fourth embodiments.

The calculation circuit 103 may have any of the configurations that have already been described for the first to fourth embodiments. For example, the calculation circuit 103 may be an arithmetic section which forms part of the computer 25.

The decision circuit 200 may have any of the configurations that have already been described for the first to fourth embodiments. For example, the decision circuit 200 may be an arithmetic section which forms part of the computer 25.

Furthermore, the measuring apparatus of this fifth embodiment may have any of the following configurations that have already been described for the first to fourth embodiments.

For example, in the measuring apparatus of this fifth embodiment, if the difference between the first and second concentrations is less than a predetermined value, the decision circuit may decide that the equilibrium has been established between a concentration of the test substance inside of the blood vessel and a concentration of the test substance measured at a position inside of the organism but outside of the blood vessel of the organism.

Also, in the measuring apparatus of this fifth embodiment, if the decision circuit decides that the equilibrium has been established, a measured value of the first concentration may be output as the concentration of the test substance in the organism.

Furthermore, in the measuring apparatus of this fifth embodiment, if the difference between the first and second concentrations is equal to or greater than a predetermined value, the decision circuit may decide that the equilibrium has not been established yet between a concentration of the test substance inside of the blood vessel and a concentration of the test substance measured at a position inside of the organism but outside of the blood vessel of the organism.

Furthermore, in the measuring apparatus of this fifth embodiment, if the decision circuit decides that the equilibrium has not been established yet, notification may be made that the concentration of the test substance in the blood vessel is now changing steeply.

Furthermore, in the measuring apparatus of this fifth embodiment, if the decision circuit decides that the equilibrium has not been established yet, a measured value of the first concentration may be output provisionally as a concentration of the test substance in the organism, and notification may be made that the measured value of the first concentration output is a provisional value.

Furthermore, the measuring apparatus of this fifth embodiment may further include a heater. If the decision circuit decides that the equilibrium has not been established yet, the heater may heat a region surrounding the positions A and B.

The heater may include the heater 35 that has been described for the fourth embodiment.

Furthermore, in the measuring apparatus of this fifth embodiment, in each of the first and second sensors, a metal pattern may have been formed on their side to be irradiated with the irradiating light. The irradiating light may be light which induces localized surface plasmon resonance in the metal pattern. The first returning light beam may be a first surface enhanced Raman scattered light beam which has been produced in the vicinity of the metal pattern of the first sensor. The first concentration may be calculated based on the radiant intensity of the first surface enhanced Raman scattered light beam. The second returning light beam may be a second surface enhanced Raman scattered light beam which has been produced in the vicinity of the metal pattern of the second sensor. And the second concentration may be calculated based on the radiant intensity of the second surface enhanced Raman scattered light beam.

Furthermore, in the measuring apparatus of this fifth embodiment, the first and second returning light beams may be surface enhanced Raman scattered light beams which have been produced by the test substance that is present in the vicinity of the metal pattern.

Furthermore, in the measuring apparatus of this fifth embodiment, a trapping substance to trap the test substance may be immobilized on the respective metal patterns of the first and second sensors.

Furthermore, in the measuring apparatus of this fifth embodiment, the first and second returning light beams may be surface enhanced Raman scattered light beams which have been produced by the trapping substance that is present in the vicinity of the metal pattern.

Furthermore, in the measuring apparatus of this fifth embodiment, the first sensor may be a first fluorescent fine particle. The second sensor may be a second fluorescent fine particle. The first and second fluorescent fine particles may produce fluorescent light, of which the radiant intensity changes in reaction to the test substance in the organism, when irradiated with the irradiating light. The irradiating light may be light, of which the wavelength is tuned to the absorption wavelength of the fluorescent fine particles. The first returning light beam may be a first fluorescent light beam which has been produced in the vicinity of the first fluorescent fine particle. The first concentration may be calculated based on the radiant intensity of the first fluorescent light beam. The second returning light beam may be a second fluorescent light beam which has been produced in the vicinity of the second fluorescent fine particle. And the second concentration may be calculated based on the radiant intensity of the second fluorescent light beam.

Furthermore, in the measuring apparatus of this fifth embodiment, the first and second sensors may be embedded in the dermis of the organism.

Furthermore, in the measuring apparatus of this fifth embodiment, the test substance may be a substance which diffuses out of the blood vessel of the organism from inside of it. For example, the test substance may be glucose.

In the first through fifth embodiments, examples of the test substances include glucose, lactic acid, pyruvic acid, acetoacetic acid, and 3-hydroxy butyric acid ($\beta$-hydroxy butyric acid).

Also, in the first through fifth embodiments, the irradiation unit for emitting the irradiating light may be configured to irradiate the first and second sensors with irradiating light beams by splitting the irradiating light emitted from a single light source into multiple light beams, for example.

Furthermore, in the first through fifth embodiments, the optical system which may be included in the detector does not have to be implemented as a group of lenses. Alternatively, the optical system may also be implemented as a wave guide.

A measuring apparatus according to the fifth embodiment can measure the concentration of a test substance in an organism by being controlled by the measuring method that has already been described for the first through fourth embodiments. The measuring method described for the first through fourth embodiments may also be carried out by getting the measuring apparatus controlled under the instructions from the measurement system 100 or the decision circuit 200. For example, the measuring method described for the first through fourth embodiments may also be carried out by getting the measuring apparatus controlled under the instruction from an arithmetic section which forms part of the computer 25.

Furthermore, in the first through fifth embodiments, the returning light for use to calculate the concentration does not have to be surface enhanced Raman scattered light or fluorescent light. Alternatively, the Raman scattered light or reflected light coming from the sensors embedded in an organism may also be used as the returning light. The returning light may be any kind of light based on which the concentration of the test substance is calculable.

Furthermore, in the measuring step and measurement system of the embodiments described above, the concentrations of a test substance at respective positions may be measured based on transmitted light that has been transmitted through the organism without using the sensors embedded in the organism.

Furthermore, in the first through fifth embodiments described above, the concentrations of a test substance at Positions A and B may be measured simultaneously. Or as long as decision can be made appropriately whether or not an equilibrium has been established yet, the concentrations of the test substance at Positions A and B may be measured at different timings, too.

Furthermore, in the first through fifth embodiments described above, a concentration of the test substance at Position C, which is a located inside of the organism but outside of the blood vessel and which is different from Positions A and B, may be measured as a third concentration. In this case, if the decision circuit has decided that the equilibrium has already been established, the measured value of the third concentration may be output as the concentration of the test substance in the organism.

A third sensor may be arranged at Position C. In that case, the third concentration may be measured by the third sensor on the same principle as the first and second sensors.

A method for measuring a biogenic component according to an embodiment of the present disclosure and a measuring apparatus for use to carry out such a method contribute to increasing the degree of reliability of the measured value. An embodiment of the present disclosure is applicable effectively to a method for measuring the concentration of a test substance included in a body fluid by embedding sensors in an organism, for example.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An apparatus for measuring the concentration of a test substance in an organism, the apparatus comprising:
    a first sensor which is configured to be arranged at a position A, the position A is located inside of the organism but outside of a blood vessel of the organism;
    a second sensor which is configured to be arranged at a position B, the position B is located inside of the organism but outside of the blood vessel of the organism, and is located more distant from the blood vessel than the position A;
    an irradiation unit which irradiates the first and second sensors with irradiating light;
    a detector which detects a first returning light beam that has returned from around the first sensor and a second returning light beam that has returned from around the second sensor;
    a calculation circuit which calculates first and second concentrations based on the first and second returning light beams, respectively, and the first and second concentrations are concentrations of the test substance at the positions A and B, respectively; and
    a decision circuit which determines, based on the first and second concentrations, whether or not an equilibrium has been established yet between a concentration of the test substance inside of the blood vessel and a concentration of the test substance measured at a position inside of the organism but outside of the blood vessel of the organism,
    wherein when the difference between the first and second concentrations is less than a predetermined value, the decision circuit decides that the equilibrium has already been established between the concentration of the test substance inside of the blood vessel and the concentration of the test substance measured at the position inside of the organism but outside of the blood vessel of the organism.

2. The apparatus of claim 1, wherein when the decision circuit decides that the equilibrium has already been established, a measured value of the first concentration is output as the concentration of the test substance in the organism.

3. The apparatus of claim 1, wherein when the difference between the first and second concentrations is equal to or greater than a predetermined value, the decision circuit decides that the equilibrium has not been established yet between the concentration of the test substance inside of the blood vessel and the concentration of the test substance measured at the position inside of the organism but outside of the blood vessel of the organism.

4. The apparatus of claim 3, wherein when the decision circuit decides that the equilibrium has not been established yet, notification is made that the concentration of the test substance in the blood vessel is now changing steeply.

5. The apparatus of claim 3, wherein when the decision circuit decides that the equilibrium has not been established yet, a measured value of the first concentration is output provisionally as a concentration of the test substance in the organism, and
    notification is made that the measured value of the first concentration output is a provisional value.

6. The apparatus of claim 3, further comprising a heater, wherein when the decision circuit decides that the equilibrium has not been established yet, the heater heats a region surrounding the positions A and B.

7. The apparatus of claim 1, wherein in each of the first and second sensors, a metal pattern has been formed on a side of the first and second sensors to be irradiated with the irradiating light,
    the irradiating light is light which induces localized surface plasmon resonance in the metal pattern,
    the first returning light beam is a first surface enhanced Raman scattered light beam which has been produced in the vicinity of the metal pattern of the first sensor,
    the first concentration is calculated based on the radiant intensity of the first surface enhanced Raman scattered light beam,
    the second returning light beam is a second surface enhanced Raman scattered light beam which has been produced in the vicinity of the metal pattern of the second sensor, and
    the second concentration is calculated based on the radiant intensity of the second surface enhanced Raman scattered light beam.

8. The apparatus of claim 7, wherein the first and second surface enhanced Raman scattered light beams are surface enhanced Raman scattered light beams which have been produced by the test substance that is present in the vicinity of the metal pattern.

9. The apparatus of claim 7, wherein a trapping substance to trap the test substance is immobilized on the respective metal patterns of the first and second sensors.

10. The apparatus of claim 9, wherein the first and second surface enhanced Raman scattered light beams are surface enhanced Raman scattered light beams which have been produced by the trapping substance that is present in the vicinity of the metal pattern.

11. The apparatus of claim 1, wherein the first sensor is a first fluorescent fine particle,
    the second sensor is a second fluorescent fine particle,
    the first and second fluorescent fine particles produce fluorescent light, of which the radiant intensity changes in reaction to the test substance in the organism, when irradiated with the irradiating light, the irradiating light is light, of which the wavelength is tuned to the absorption wavelength of the first and second fluorescent fine particles, the first returning light beam is a first fluorescent light beam which has been produced in the vicinity of the first fluorescent fine particle, the first concentration is calculated based on the radiant intensity of the first fluorescent light beam, the second returning light beam is a second fluorescent light beam which has been produced in the vicinity of the second fluorescent fine particle, and the second concentration is calculated based on the radiant intensity of the second fluorescent light beam.

12. The apparatus of claim 1, wherein the first and second sensors are configured to be embedded in the dermis of the organism.

13. The apparatus of claim 1, wherein the test substance is glucose.

14. The apparatus of claim 1, wherein the position B is configured to be located shallower in a depth direction of the organism than the position A.

15. A method for measuring the concentration of a test substance in an organism, the method comprising the steps of:

(a) measuring first and second concentrations using first and second sensors, respectively, that are concentrations of the test substance at positions A and B, respectively, wherein the first sensor is configured to be arranged at the position A, the position A is located inside of the organism but outside of a blood vessel of the organism, and the second sensor is configured to be arranged at the position B, the position B is located inside of the organism but outside of the blood vessel of the organism, and is located more distant from the blood vessel than the position A;

(b) irradiating, via an irradiation unit, the first and second sensors with irradiating light;

(c) detecting, via a detector, a first returning light beam that has returned from around the first sensor and a second returning light beam that has returned from around the second sensor;

(d) calculating, via a calculation circuit, the first and second concentrations based on the first and second returning light beams, respectively, and the first and second concentrations are concentrations of the test substance at the positions A and B, respectively; and (e) determining, via a decision circuit, based on the first and second concentrations, whether or not an equilibrium has been established yet between a concentration of the test substance inside of the blood vessel and a concentration of the test substance measured at a position inside of the organism but outside of the blood vessel of the organism, wherein when the difference between the first and second concentrations is less than a predetermined value, the decision circuit decides that the equilibrium has already been established between the concentration of the test substance inside of the blood vessel and the concentration of the test substance measured at the position inside of the organism but outside of the blood vessel of the organism.

16. The method of claim 15, wherein the position B is configured to be located shallower in a depth direction of the organism than the position A.

* * * * *